(12) United States Patent
Freel Meyers et al.

(10) Patent No.: US 9,930,893 B2
(45) Date of Patent: Apr. 3, 2018

(54) INHIBITORS OF DXP SYNTHASE AND METHODS OF USE THEREOF

(71) Applicant: The Johns Hopkins University, Baltimore, MD (US)

(72) Inventors: Caren L. Freel Meyers, Towson, MD (US); Francine Morris, Philadelphia, PA (US); Ryan J. Vierling, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/618,589

(22) Filed: Feb. 10, 2015

(65) Prior Publication Data

US 2015/0225430 A1   Aug. 13, 2015

Related U.S. Application Data

(60) Provisional application No. 61/938,114, filed on Feb. 10, 2014.

(51) Int. Cl.
| | | |
|---|---|---|
| *A01N 57/22* | (2006.01) | |
| *C07F 9/40* | (2006.01) | |
| *A01N 57/20* | (2006.01) | |
| *C07F 9/6539* | (2006.01) | |

(52) U.S. Cl.
CPC ............ *A01N 57/22* (2013.01); *C07F 9/4065* (2013.01); *C07F 9/4078* (2013.01); *C07F 9/4087* (2013.01); *C07F 9/6539* (2013.01)

(58) Field of Classification Search
CPC ..... A01N 57/22; C07F 9/4065; C07F 9/4078; C07F 9/4087; C07F 9/6539
See application file for complete search history.

(56) References Cited

U.S. PATENT DOCUMENTS

2011/0045025 A1\*  2/2011  Middaugh ............ A61K 9/0019
                                                        424/239.1

OTHER PUBLICATIONS

Smith et al., "Selective inhibition of E. coli 1-deoxy-D-xyulose-5-phosphate synthase by acetylphosphonates," 2012; Med. Chem. Commun., 3:65-67.*
Brammer et al., "1-Deoxy-D-xyulose-5-Phosphate Synthase Catalyzes a Novel Random Sequential Mechanism", 2011; J. of Biological Chemistry, 286(42):36522-36531.*
Morris et al., "DXP Synthase-Catalyzed C—N Bond Formation: Nitroso Substrate Specificity Studies Guide Selective Inhibitor Design," 2013; ChemBioChem 14:1309-1315.*
Smith, Jessica M.; et al. "Selective inhibition of E. coli 1-deoxy-D-xylulose-5-phosphate synthase by acetylphosphonates" Med. Chem. Commun., 2012, v 3. 65-67 and Supporting information.*
Khomutov, R. M. ; et. al. "Synthesis of a-ketophosphonic acids" Scifinder Abstract.*
Morris, F.; et al. "DXP Synthase-Catalyzed C N Bond Formation: Nitroso Substrate Specificity Studies Guide Selective Inhibitor Design" ChemBioChem, 2013, 14(11), 1309-1315.*

\* cited by examiner

*Primary Examiner* — Mina Haghighatian
*Assistant Examiner* — Erin E Hirt
(74) *Attorney, Agent, or Firm* — Mintz Levin Cohn Ferris Glovsky and Popeo, P.C.; Peter F. Corless

(57) ABSTRACT

Novel inhibitors of DXP synthase and methods of use thereof are disclosed.

2 Claims, 15 Drawing Sheets

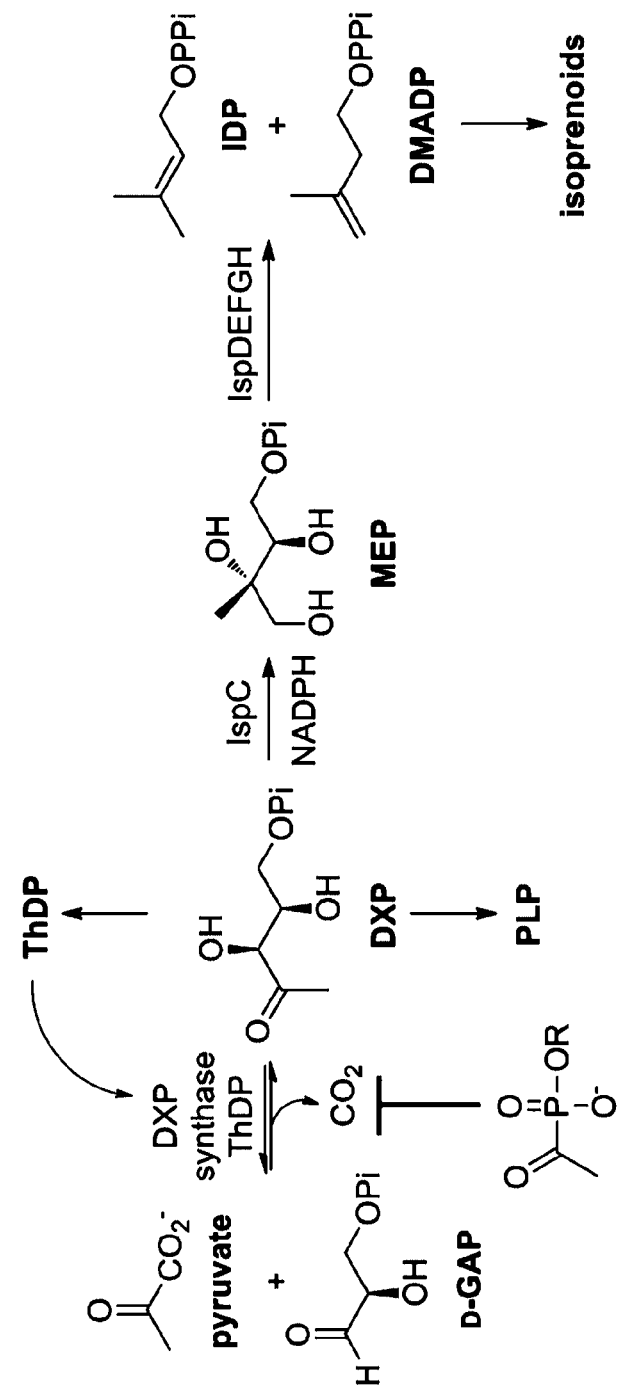
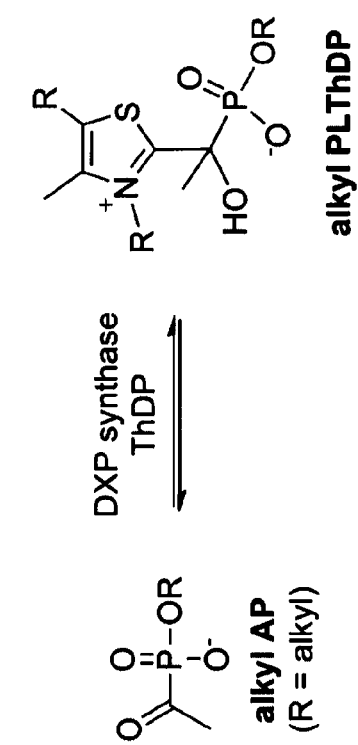
FIG. 1A
FIG. 1B

Accepted as substrates
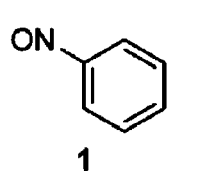 1
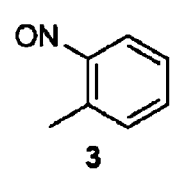 3
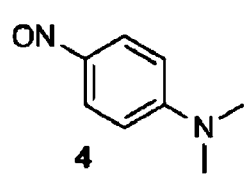 4
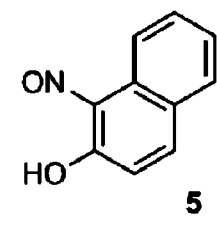 5
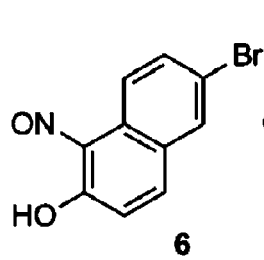 6
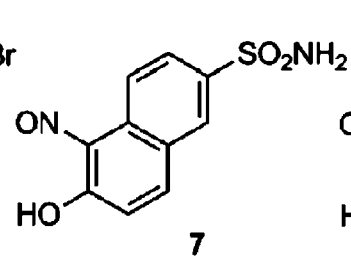 7
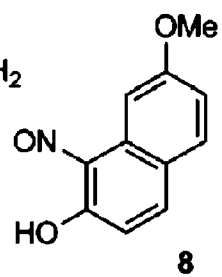 8
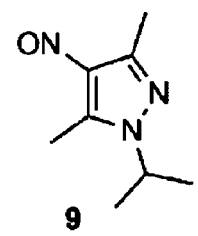 9
Not accepted as substrates
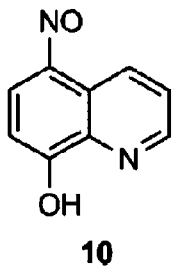 10
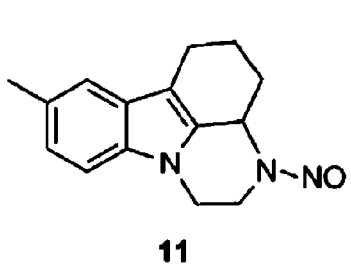 11
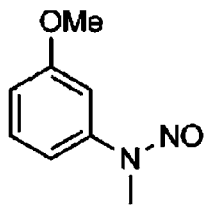 12
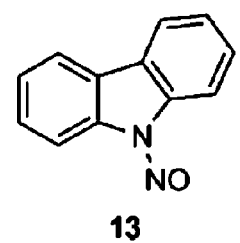 13
FIG. 2

FIG. 14A  PentAP $^1$H NMR:
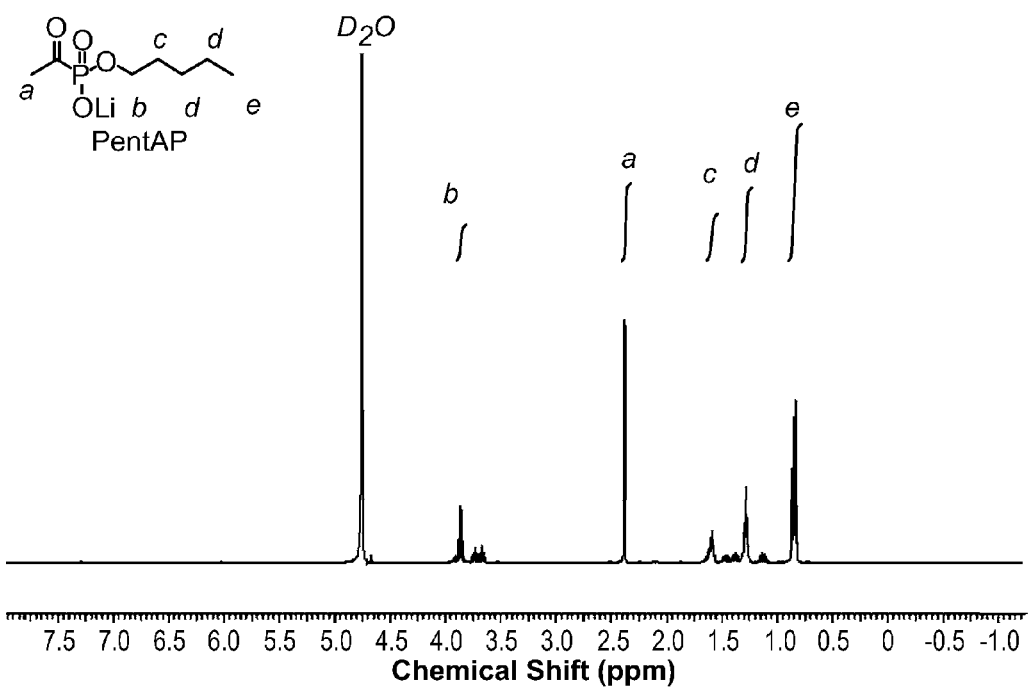
FIG. 14B  PentAP $^{31}$P NMR:
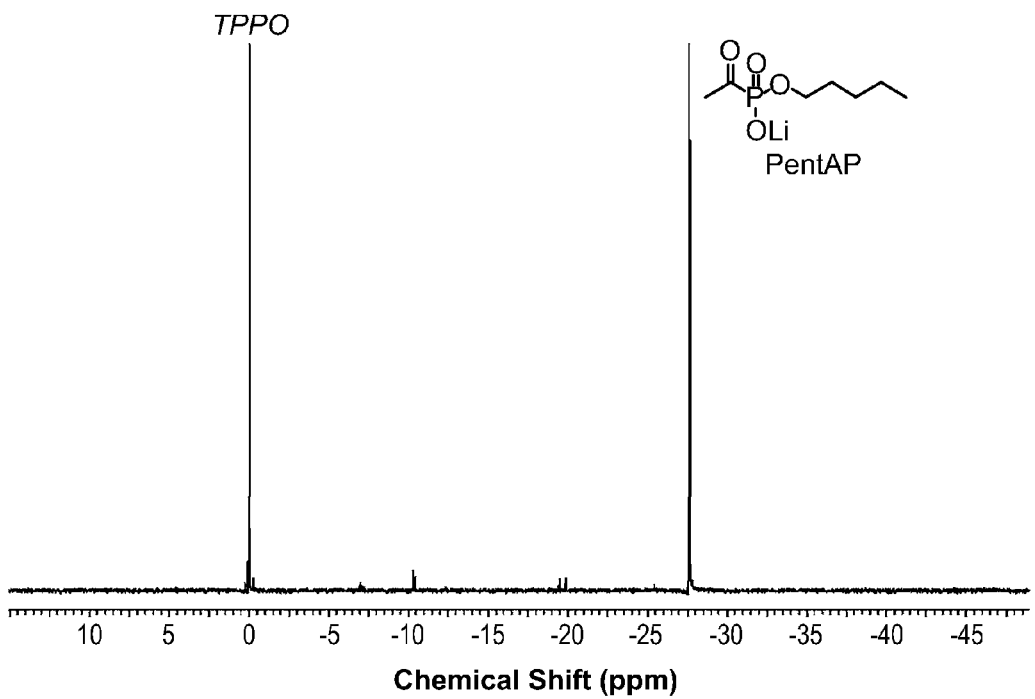

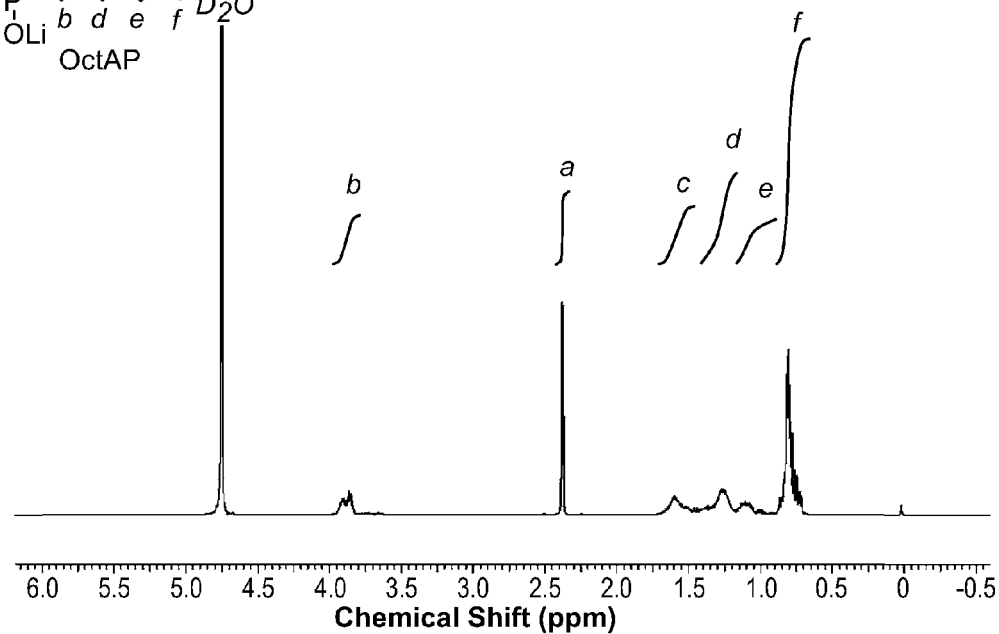
FIG. 16A OctAP $^1$H NMR:
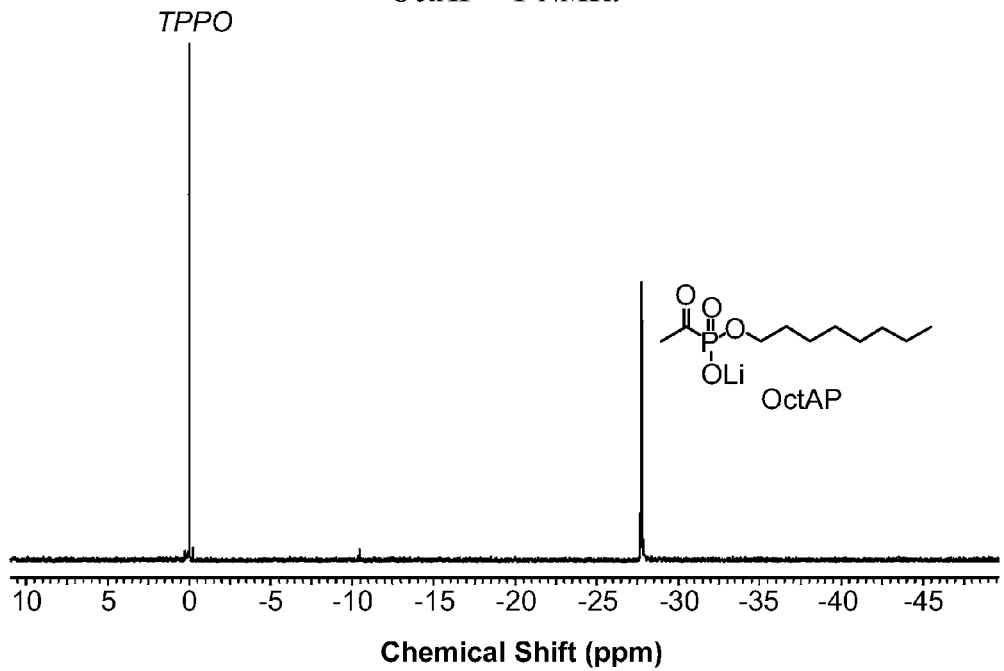
FIG. 16B OctAP $^{31}$P NMR:

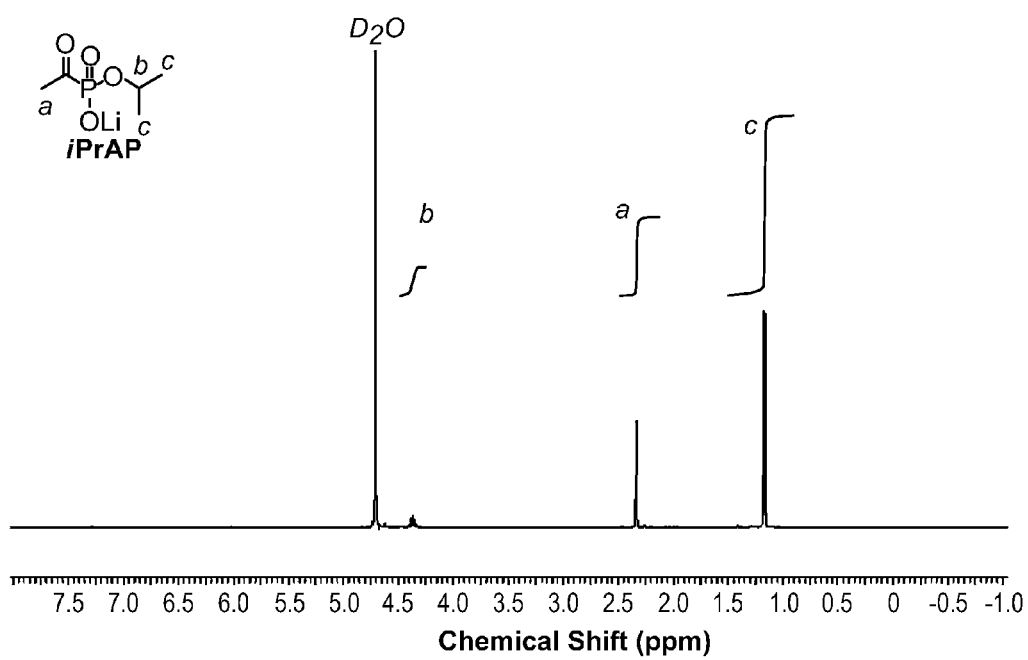
FIG. 17A  iPrAP $^1$H NMR:
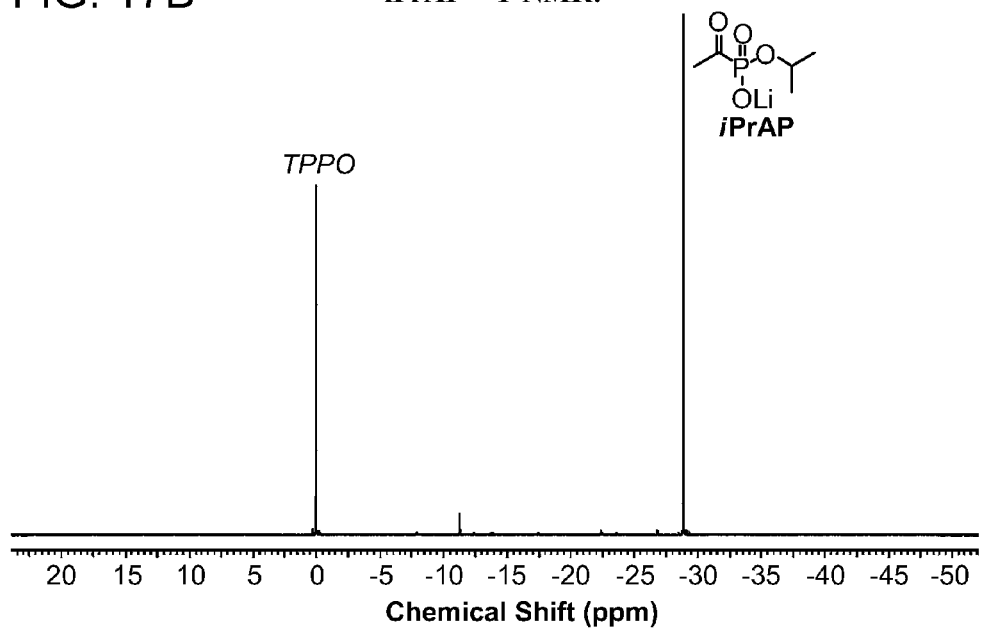
FIG. 17B  iPrAP $^{31}$P NMR:

INHIBITORS OF DXP SYNTHASE AND METHODS OF USE THEREOF

CROSS REFERENCE TO RELATED APPLICATION

The present application claims priority to U.S. Provisional Application No. 61/938,114, filed Feb. 10, 2014, the entire contents of which is incorporated herein for all purposes by this reference.

STATEMENT OF RIGHTS TO INVENTIONS MADE UNDER FEDERALLY SPONSORED RESEARCH

This work was supported in part by National Institutes of Health grants R01 GM084998 and T32GM08018901. The government has certain rights in the invention.

TECHNICAL FIELD

The present invention relates to a compound that inhibits bacterial methylerythritol phosphate pathways, and a use thereof.

BACKGROUND OF THE INVENTION

The rise of drug-resistant microorganisms has resulted in increasing numbers of infections that are difficult to treat with existing therapies. Although new antibiotics have been developed, problems such as toxicity and relatively narrow spectrum of activity often limit the utility of such drugs.

1-Deoxy-D-xylulose 5-phosphate (DXP) synthase catalyzes the first step in the non-mammalian isoprenoid biosynthetic pathway (FIG. 1A) to form DXP from pyruvate and D-glyceraldehyde 3-phosphate (D-GAP) in a thiamin diphosphate-dependent manner (FIG. 1A). Its unique structure and mechanism distinguish DXP synthase from its homologs, suggesting it could be pursued as an anti-infective drug target. However, few reports describe development of selective inhibitors of this enzyme.

SUMMARY OF THE INVENTION

In one aspect, the invention provides a compound represented by the formula:

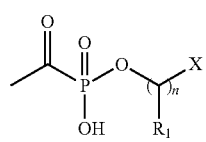

(I)

in which

X is an optionally substituted aryl or heteroaryl group, a linear or branched $C_3$-$C_8$ alkyl group, a $C_3$-$C_6$ alkenyl group, or a cycloalkyl or heterocyclic group having 3-7 atoms in the ring moiety;

$R_1$, independently for each occurrence, is absent, or if present, is halo or optionally substituted $C_1$-$C_4$ alkyl;

or $R_1$, taken together with a substituent on the substituted aryl or heteroaryl group of X, forms a 5- or 6-membered carbocyclic or heterocyclic ring; and n is 0, 1, 2 or 3;

or a pharmaceutically acceptable salt thereof.

In certain embodiments, X is

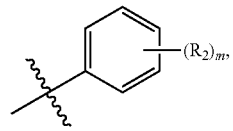

in which $R_2$ is halogen, hydroxy, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, —C(O)$C_1$-$C_6$alkyl, —C(O)$C_1$-$C_6$alkoxy, —C(O)(mono- or di-($C_1$-$C_6$alkyl)amino), ($C_3$-$C_7$cycloalkyl)$C_0$-$C_4$alkyl, mono- or di-($C_1$-$C_6$alkyl)amino, and mono- or di-($C_1$-$C_6$alkyl)aminosulfonyl, and m is an integer from 1-5.

In certain embodiments, n is 1 or 2.

In certain embodiments, $R_1$ is H for each occurrence.

In certain embodiments, one occurrence of $R_1$, taken together with a substituent on the X group, forms a 5- or 6-membered carbocyclic or heterocyclic ring.

In certain embodiments, X is an optionally substituted aryl group.

In certain embodiments, the compound is represented by the formula:

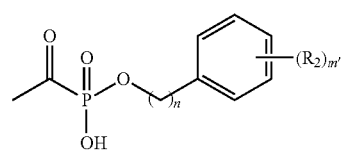

(II)

in which $R_2$ is halogen, hydroxy, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, —C(O)$C_1$-$C_6$alkyl, —C(O)$C_1$-$C_6$alkoxy, —C(O)(mono- or di-($C_1$-$C_6$alkyl)amino), ($C_3$-$C_7$cycloalkyl)$C_0$-$C_4$alkyl, mono- or di-($C_1$-$C_6$alkyl)amino, and mono- or di-($C_1$-$C_6$alkyl)aminosulfonyl;

m' is an integer from 0-5; and n is 0, 1, 2 or 3.

In certain embodiments, $R_2$ is $C_1$-$C_6$alkoxy and m' is 1.

In certain embodiments, the compound is selected from the group consisting of:

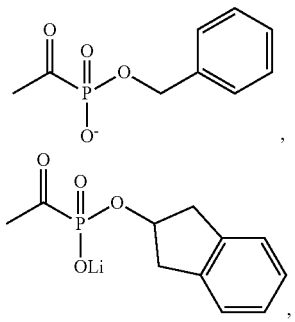"

-continued

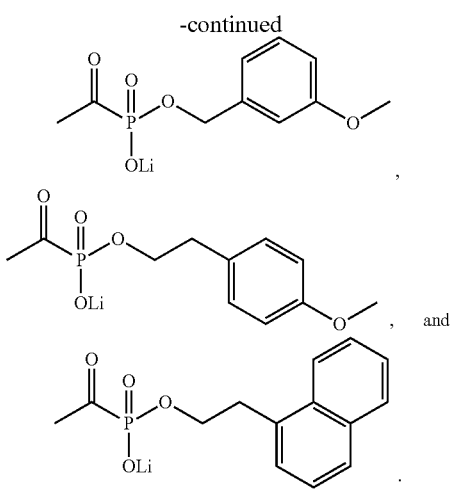

, and

In certain embodiments, X is a linear or branched $C_3$-$C_8$ alkyl group.

In certain embodiments, n is 0 or 1.

In certain embodiments, the compound is selected from the group consisting of:

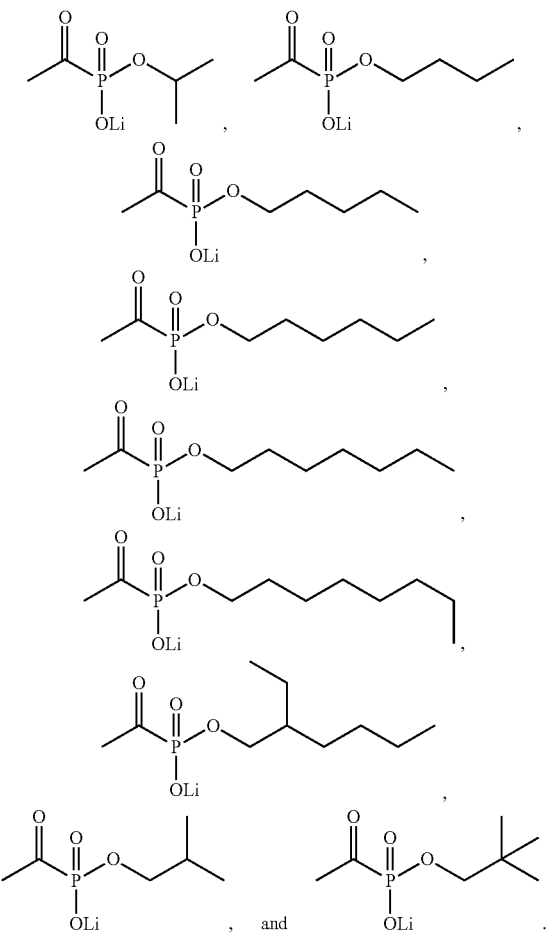

, and

In another aspect, the invention provide a method of inhibiting 1-deoxy-D-xylulose-5-phosphate synthase (e.g., in vivo or in vitro), the method comprising contacting 1-deoxy-D-xylulose-5-phosphate synthase with a compound or salt of a compound of the invention.

In certain embodiments, the 1-deoxy-D-xylulose-5-phosphate synthase is contacted with a compound or salt of the invention in vitro or in vivo.

In certain embodiments, the 1-deoxy-D-xylulose-5-phosphate synthase is a bacterial 1-deoxy-D-xylulose-5-phosphate synthase.

In certain embodiments, the compound or salt of the invention is at least about 30-fold selective for 1-deoxy-D-xylulose-5-phosphate synthase over a mammalian ThDP-dependent enzyme.

In another aspect, the invention provides a method of inhibiting isoprenoid biosynthesis in a microorganism, the method comprising contacting the microorganism with a compound or salt of the invention.

In another aspect, the invention provides a method of inhibiting growth of a bacterial cell, the method comprising contacting the bacterial cell with a compound or salt of the invention.

In another aspect, the invention provides a method of inhibiting growth of a plant, the method comprising contacting the plant with a compound or salt of the invention.

In another aspect, the invention provides a method of inhibiting growth of a plant cell, the method comprising contacting the plant cell with a compound or salt of the invention.

In another aspect, the invention provides a method of inhibiting growth of a parasite, the method comprising contacting the parasite with a compound or salt of the invention.

In another aspect, the invention provides a pharmaceutical composition comprising a compound of the invention, together with a pharmaceutically acceptable carrier.

Other aspects and embodiments of the invention will be apparent from the description herein.

BRIEF DESCRIPTION OF THE DRAWINGS

FIG. 1A shows an isoprenoid biosynthesis in human pathogens via the methylerythritol phosphate pathway; and FIG. 1B shows that alkylacetylphosphonates (alkyl AP) are competitive inhibitors with respect to pyruvate and act via formation of a phosphonolactyl thiamin diphosphate intermediate (PLThDP).

FIG. 2 shows exemplary nitroso substrate usage by DXP synthase.

FIG. 3A) Design of BnAP as a selective inhibitor of DXP synthase. FIG. 3B) BnAP is a competitive inhibitor of DXP synthase with respect to pyruvate ($K_i$=10.4±1.3 μM). The concentration of pyruvate was varied (20-200 μM) at several fixed concentrations of BnAP (0 (○), 15 (●), 30 (□) and 60 (■) μM) and 100 μM D-GAP; FIG. 3C) BnAP is an uncompetitive inhibitor of DXP synthase with respect to D-GAP ($K_i$=70±8 μM). The concentration of D-GAP was varied (10-120 μM) at fixed concentrations of BnAP (0 (○), 25 (●), 50 (□) and 75 (■) μM) and 200 μM pyruvate; FIG. 3D) BnAP is a competitive inhibitor of PDH with respect to pyruvate and exhibits selective inhibition against DXP synthase compared to PDH ($K_i^{PDH}$=882±78 μM, $K_i^{PDH}/K_i^{DXPS}$~85). The concentration of pyruvate was varied (20-200 μM) at several fixed concentrations of BnAP (0 (○), 0.5 (●), 1 (□) and 2.25 (■) mM).

FIG. 4A), hexylacetylphosphonate (HexAP; FIG. 4B), and octylacetyl phosphonate (OctAP; FIG. 4C). Inhibition assays were performed as previously described[18, 40]. D-GAP was held constant at 140 μM. Pyruvate concentration was varied from 12-240 μM and acetylphosphonate concentration was varied: 0 μM (○), 10 μM (●), 25 μM (□) and 50 μM (■). Experiments were performed in triplicate, and data were subjected to non-linear regression analysis for $K_i$ determinations (GraphPad Prism). Representative Lineweaver-Burk plots (GraFit from Erithacus Software) are shown for PentAP (FIG. 4A), HexAP (FIG. 4B) and OctAP (FIG. 4C) to illustrate the competitive inhibition mode with respect to pyruvate.

FIG. 14A and FIG. 14B are NMR characterization of PentAP by $^1$H NMR (FIG. 14A) and $^{31}$P NMR (FIG. 14B).

FIG. 16A and FIG. 16B are NMR characterization of OctAP by $^1$H NMR (FIG. 16A) and $^{31}$P NMR (FIG. 16B).

FIG. 17A and FIG. 17B are NMR characterization of iPrAP by $^1$H NMR (FIG. 17A) and $^{31}$P NMR (FIG. 17B).

DETAILED DESCRIPTION OF THE INVENTION

Figure 3A:
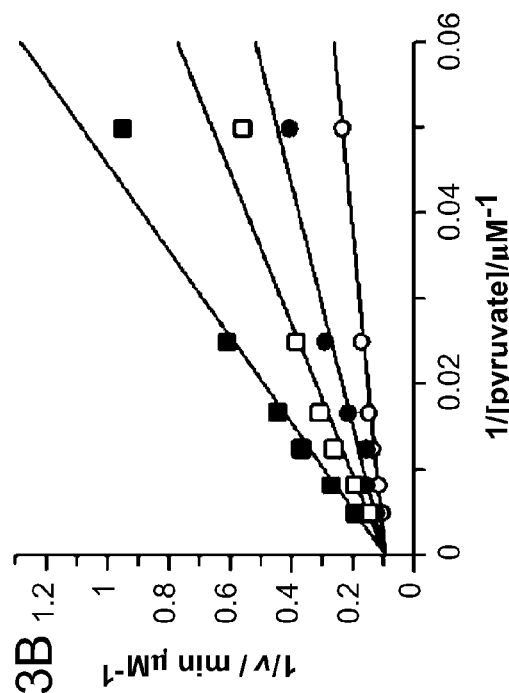
FIG. 3A, FIG. 3B, FIG. 3C and FIG. 3D are charts showing that benzyl acetyl phosphonate (BnAP) is a selective inhibitor of DXP synthase. BnAP is a selective inhibitor of DXP synthase. Representative double reciprocal plots are shown.
Figure 3C:
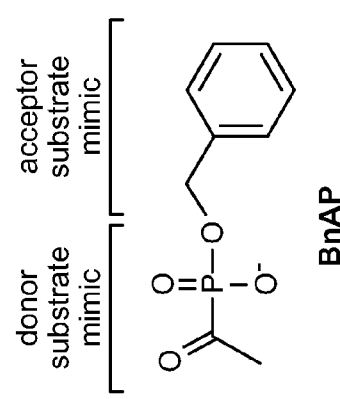
Figure 3B:
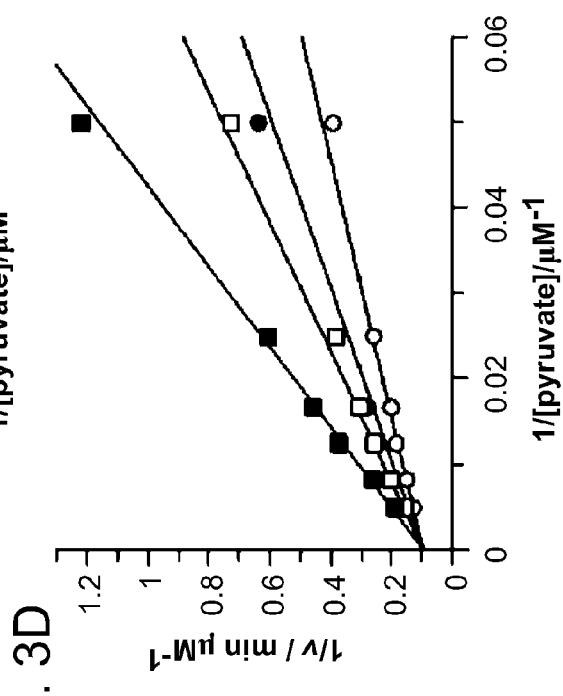
Figure 3D:
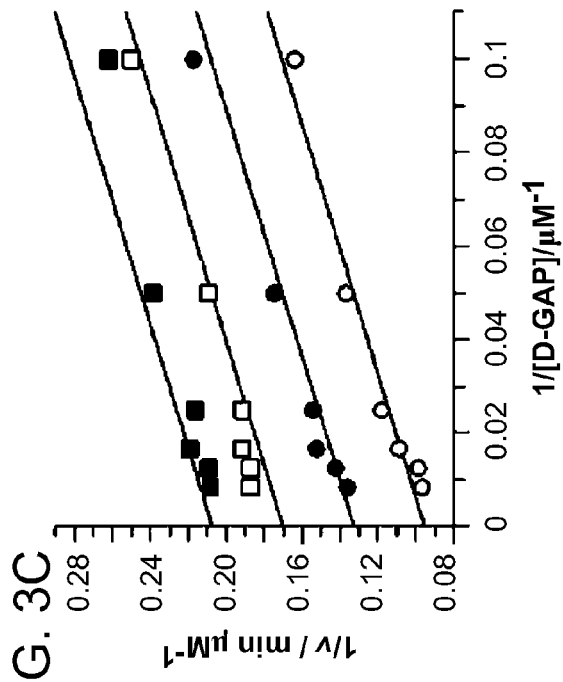

The present invention relates to novel inhibitors of 1-deoxy-D-xylulose-5-phosphate synthase and methods of making and using such compounds.

In one aspect, the invention provides a compound represented by the formula:

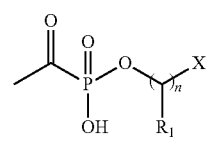

(I)

in which

X is an optionally substituted aryl or heteroaryl group, a linear or branched $C_3$-$C_8$ alkyl group, a $C_3$-$C_6$ alkenyl group, or a cycloalkyl or heterocyclic group having 3-7 atoms in the ring moiety;

$R_1$, independently for each occurrence, is absent, or if present, is halo or optionally substituted $C_1$-$C_4$ alkyl;

or $R_1$, taken together with a substituent on the substituted aryl or heteroaryl group of X, forms a 5- or 6-membered carbocyclic or heterocyclic ring; and n is 0, 1, 2 or 3;

or a pharmaceutically acceptable salt thereof.

In certain embodiments, X is

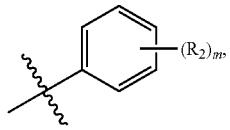

in which $R_2$ is halogen, hydroxy, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, —C(O)$C_1$-$C_6$alkyl, —C(O)$C_1$-$C_6$alkoxy, —C(O)(mono- or di-($C_1$-$C_6$alkyl)amino), ($C_3$-$C_7$cycloalkyl)$C_0$-$C_4$alkyl, mono- or di-($C_1$-$C_6$alkyl)amino, and mono- or di-($C_1$-$C_6$alkyl)aminosulfonyl, and m is an integer from 1-5.

In certain embodiments, n is 1 or 2.

In certain embodiments, $R_1$ is H for each occurrence.

In certain embodiments, one occurrence of $R_1$, taken together with a substituent on the X group, forms a 5- or 6-membered carbocyclic or heterocyclic ring.

In certain embodiments, X is an optionally substituted aryl group.

In certain embodiments, $R_2$ is optionally substituted $C_1$-$C_6$alkyl.

In certain embodiments, the compound is represented by the formula:

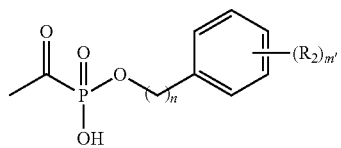

(II)

in which $R_2$ is halogen, hydroxy, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, —C(O)$C_1$-$C_6$alkyl, —C(O)$C_1$-$C_6$alkoxy, —C(O)(mono- or di-($C_1$-$C_6$alkyl)amino), ($C_3$-$C_7$cycloalkyl)$C_0$-$C_4$alkyl, mono- or di-($C_1$-$C_6$alkyl)amino, and mono- or di-($C_1$-$C_6$alkyl)aminosulfonyl;

m' is an integer from 0-5; and n is 0, 1, 2 or 3.

In certain embodiments, $R_2$ is $C_1$-$C_6$alkoxy and m' is 1.

In certain embodiments, X is a linear or branched $C_3$-$C_8$ alkyl group.

In certain embodiments, n is 0 or 1.

In certain embodiments, the compound is selected from the group consisting of:

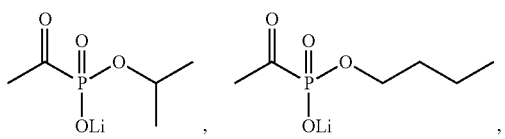

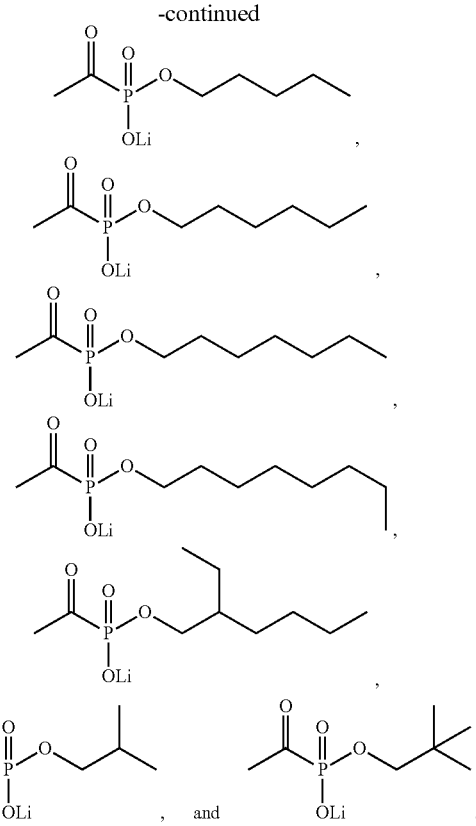

In another aspect, the invention provides a method of inhibiting 1-deoxy-D-xylulose-5-phosphate synthase, the method comprising contacting 1-deoxy-D-xylulose-5-phosphate synthase with a compound or salt of the invention. In certain embodiments, the 1-deoxy-D-xylulose-5-phosphate synthase is contacted with a compound or salt of the invention in vitro or in vivo. In certain embodiments, the 1-deoxy-D-xylulose-5-phosphate synthase is a bacterial 1-deoxy-D-xylulose-5-phosphate synthase.

In certain embodiments, the compound or salt of the invention is at least about 10-fold (or about 20-fold, 30-fold, 50-fold, 100-fold, 500-fold, or 1000-fold) selective for 1-deoxy-D-xylulose-5-phosphate synthase over a mammalian ThDP-dependent enzyme.

In another aspect, the invention provides a method of inhibiting isoprenoid biosynthesis in a microorganism, the method comprising contacting the microorganism with a compound or salt of the invention.

In another aspect, the invention provides a method of inhibiting growth of a bacterial cell, the method comprising contacting the bacterial cell with a compound or salt of the invention.

In another aspect, the invention provides a method of inhibiting growth of a plant, the method comprising contacting the plant with a compound or salt of the invention.

In another aspect, the invention provides a method of inhibiting growth of a plant cell (in vivo or in vitro), the method comprising contacting the plant cell with a compound or salt of the invention.

In another aspect, the invention provides a pharmaceutical composition comprising a compound of the invention, together with a pharmaceutically acceptable carrier.

Definitions

Listed below are definitions of various terms used to describe this invention. These definitions apply to the terms as they are used throughout this specification and claims, unless otherwise limited in specific instances, either individually or as part of a larger group.

The term "alkyl," as used herein, refers to saturated, straight- or branched-chain hydrocarbon radicals containing, in certain embodiments, between one and six ($C_1$-$C_6$), or one and eight ($C_1$-$C_8$)carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "alkenyl," as used herein, denotes a monovalent group derived from a hydrocarbon moiety containing, in certain embodiments, from two to six ($C_2$-$C_6$), or two to eight ($C_2$-$C_8$) carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkynyl," as used herein, denotes a monovalent group derived from a hydrocarbon moiety containing, in certain embodiments, from two to six, or two to eight carbon atoms having at least one carbon-carbon triple bond. The alkynyl group may or may not be the point of attachment to another group. Representative alkynyl groups include, but are not limited to, for example, ethynyl, 1-propynyl, 1-butynyl, heptynyl, octynyl and the like.

The term "alkoxy" refers to an —O-alkyl radical.

The term "aryl," as used herein, refers to a mono- or poly-cyclic carbocyclic ring system having one or more aromatic rings, fused or non-fused, including, but not limited to, phenyl, naphthyl, tetrahydronaphthyl, indanyl, idenyl and the like.

The term "aralkyl," as used herein, refers to an alkyl residue attached to an aryl ring. Examples include, but are not limited to, benzyl, phenethyl and the like.

The term "cycloalkyl," as used herein, denotes a monovalent group derived from a monocyclic or polycyclic saturated or partially unsaturated carbocyclic ring compound. Examples of $C_3$-$C_8$-cycloalkyl include, but not limited to, cyclopropyl, cyclobutyl, cyclopentyl, cyclohexyl, cyclopentyl and cyclooctyl; and examples of $C_3$-$C_{12}$-cycloalkyl include, but not limited to, cyclopropyl, cyclobutyl, cyclopentyl, cyclohexyl, bicyclo[2.2.1] heptyl, and bicyclo[2.2.2] octyl. Also contemplated are a monovalent group derived from a monocyclic or polycyclic carbocyclic ring compound having at least one carbon-carbon double bond by the removal of a single hydrogen atom. Examples of such groups include, but are not limited to, cyclopropenyl, cyclobutenyl, cyclopentenyl, cyclohexenyl, cycloheptenyl, cyclooctenyl, and the like.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which one ring atoms is selected from S, O and N; zero, one or two ring atoms are additional heteroatoms independently selected from S, O and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

The term "heteroaralkyl," as used herein, refers to an alkyl residue attached to a heteroaryl ring. Examples include, but are not limited to, pyridinylmethyl, pyrimidinylethyl and the like.

The term "heterocycloalkyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, and (iv) any of the above rings may be fused to a benzene ring. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl) where $C_1$-$C_{12}$ alkyl is as previously defined.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic phosphates and aliphatic phosphates. Examples of aliphatic carbonyls include, but are not limited to, acetyl, propionyl, 2-fluoroacetyl, butyryl, 2-hydroxy acetyl, and the like.

In accordance with the invention, any of the aryls, substituted aryls, heteroaryls and substituted heteroaryls described herein, can be any aromatic group. Aromatic groups can be substituted or unsubstituted.

The terms "halo" and "halogen," as used herein, refer to an atom selected from fluorine, chlorine, bromine and iodine.

The term "subject" includes mammalian and non-mammalian animals.

The term "mammal" includes a human or non-human mammal, such as a bovine, equine, canine, ovine, or feline.

The term "ThDP-dependent enzyme" refers to an enzyme that requires thiamine diphosphate (ThDP) as a co-factor for activity. Examples of such enzymes include transketolase, pyruvate decarboxylase, alpha-ketoglutarate dehydrogenase, branched-chain amino dehydrogenase, the E1 subunit of pyruvate dehydrogenase, pyruvate oxidase, pyruvate ferredoxin oxidoreductase, phenylglyoxylate dehydrogenase, oxoglutarate dehydrogenase, 3-methyl-2-oxobutanoate dehydrogenase, pyruvate synthase, 2-oxoglutarate synthase, formaldehyde transketolase, acetoin-ribose-5-phosphate transaldolase, 2-hydroxy-3-oxoadipate synthase, acetolactate cynthase, sulfoacetaldehyde acetyltransferase, N2-(2-carboxyethyl)arginine synthase, 3,5/4-trihydroxycyclohexa-1,2-dione hydrolase, tartronate-semialdehyde synthase, benzoylformate decarboxylase, 2-oxoglutarate decarboxylase, indolepyruvate decarboxylase, 5-guanidino-2-oxopentanoate decarboxylase, sulfopyruvate decarboxylase, oxalyl-CoA decarboxylase, phosphonopyruvate decarboxylase, fructose-6-phosphate phosphoketolase, benzoin aldolase, phosphoketolase, 2-oxoacid oxidoreductase, and 2-hydroxyphytanoyl-CoA lyase.

The term "bacteria", as used herein, includes bacteria expressing DXP synthase, including gram negative bacteria such as *E. coli, Yersinia pestis, Salmonella enterica, Bacillus abortus, Chlamydia trachomatis, Chlamydia pneumonia, Fransicella tularensis, Pseudomonas aeruginosa, Vibrio cholerae, Klebsiella pneumonia, Bordetella pertussis, Haemophilus influenza, Heliobacter pylori, Shigella flexneri, Shigella dysenteriae, Neisseria meningitides, Campylobacter jejuni,* and *Yersinia enterocolitica,* and gram positive bacteria such as *Mycobacterium tuberculosis, Bacillus anthracis, Bacillus subtilis, Clostridium difficile, Clostridium botulinum, Clostridium perfringens, Listeria monocytogenes* and *Nocardia terpenica.*

The term "parasite", as used herein, refers to any apicomplexan parasite (e.g., a mammalian apicomplexan parasite), including protozoa such as *Toxoplasma gondii, Cryptosporidium parvum, Cyclospora cayetanensis, Isospora belli, Babesia microti, Plasmodium falciparum, P. malariae, P. ovale* and *P. vivax.*

The term "plant", as used herein, refers to multicellular organisms of the kingdom Plantae. Plants include, grasses (including crops such as cereal crops), vegetables, trees, mosses, and the like. In certain embodiments, a plant can be a weed or other undesired plant (e.g., a non-native invasive plant).

Compounds

In one aspect, the invention provides a compound represented by the formula:

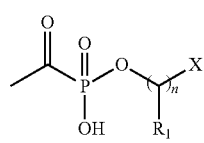

(I)

in which

X is an optionally substituted aryl or heteroaryl group, a linear or branched $C_3$-$C_8$ alkyl group, a $C_3$-$C_6$alkenyl group, or a cycloalkyl or heterocyclic group having 3-7 atoms in the ring moiety;

$R_1$, independently for each occurrence, is absent, or if present, is halo or optionally substituted $C_1$-$C_4$ alkyl;

or $R_1$, taken together with a substituent on the substituted aryl or heteroaryl group of X, forms a 5- or 6-membered carbocyclic or heterocyclic ring; and n is 0, 1, 2 or 3;

or a pharmaceutically acceptable salt thereof.

In certain embodiments, X is

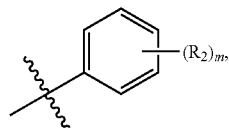

in which $R_2$ is halogen, hydroxy, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, —C(O)$C_1$-$C_6$alkyl, —C(O)$C_1$-$C_6$alkoxy, —C(O)(mono- or di-($C_1$-$C_6$alkyl)amino), ($C_3$-$C_7$cycloalkyl)$C_0$-$C_4$alkyl, mono- or di-($C_1$-$C_6$alkyl)amino, and mono- or di-($C_1$-$C_6$alkyl)aminosulfonyl, and m is an integer from 1-5.

In certain embodiments, n is 1 or 2.

In certain embodiments, $R_1$ is H for each occurrence.

In certain embodiments, one occurrence of $R_1$, taken together with a substituent on the X group, forms a 5- or 6-membered carbocyclic or heterocyclic ring.

In certain embodiments, X is an optionally substituted aryl group.

In certain embodiments, $R_2$ is optionally substituted $C_1$-$C_6$alkyl.

In certain embodiments, the compound is represented by the formula:

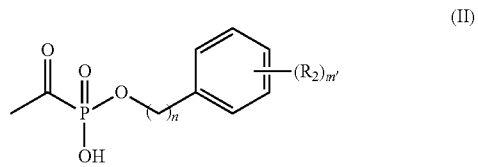

(II)

in which $R_2$ is halogen, hydroxy, cyano, amino, nitro, $C_1$-$C_6$alkyl, $C_2$-$C_6$alkenyl, $C_2$-$C_6$alkynyl, $C_1$-$C_6$haloalkyl, $C_1$-$C_6$hydroxyalkyl, $C_1$-$C_6$alkoxy, $C_1$-$C_6$haloalkoxy, —C(O)$C_1$-$C_6$alkyl, —C(O)$C_1$-$C_6$alkoxy, —C(O)(mono- or di-($C_1$-$C_6$alkyl)amino), ($C_3$-$C_7$cycloalkyl)$C_0$-$C_4$alkyl, mono- or di-($C_1$-$C_6$alkyl)amino, and mono- or di-($C_1$-$C_6$alkyl)aminosulfonyl;

m' is an integer from 0-5; and n is 0, 1, 2 or 3.

In certain embodiments, $R_2$ is $C_1$-$C_6$alkoxy and m' is 1.

In certain embodiments, the compound is selected from the group consisting of:

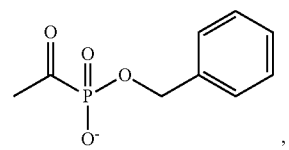

(Compound 1)

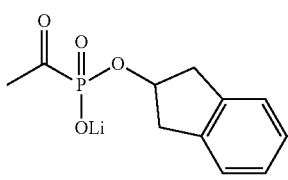

(Compound 2)

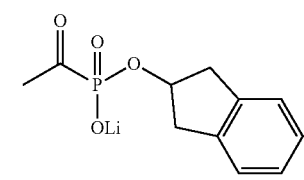

(Compound 3)

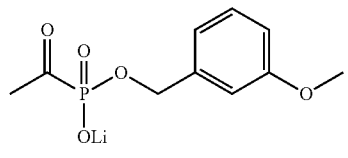

(Compound 4)

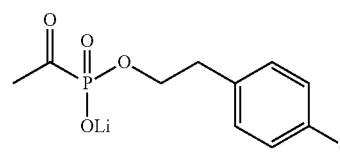

, and (Compound 5)

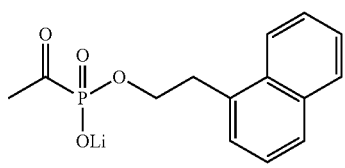

In certain embodiments, X is a linear or branched $C_3$-$C_8$ alkyl group.

In certain embodiments, n is 0 or 1.

In certain embodiments, the compound is selected from the group consisting of:

(Compound 6)

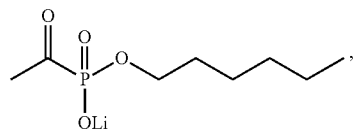

(Compound 7)

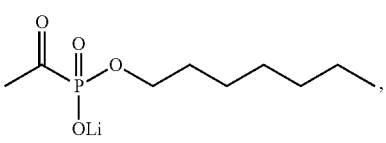

(Compound 8)

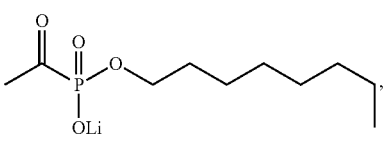

(Compound 9)

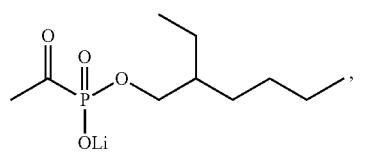

(Compound 10)

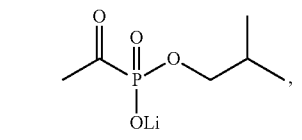

(Compound 11)

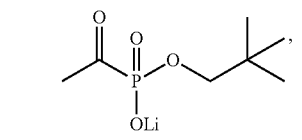

(Compound 12)

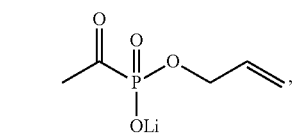

(Compound 13)

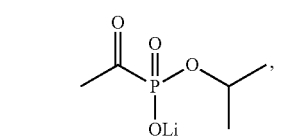

(Compound 14)

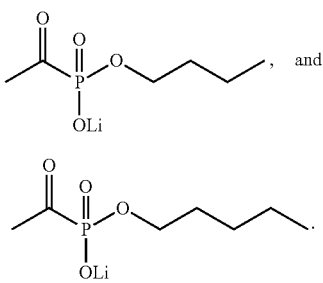, and (Compound 15)

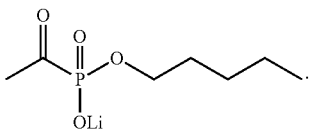.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. The terms "optionally substituted", "optionally substituted alkyl," "optionally substituted "optionally substituted alkenyl," "optionally substituted alkynyl", "optionally substituted cycloalkyl," "optionally substituted cycloalkenyl," "optionally substituted aryl", "optionally substituted heteroaryl," "optionally substituted aralkyl", "optionally substituted heteroaralkyl," "optionally substituted heterocycloalkyl," and any other optionally substituted group as used herein, refer to groups that are substituted or unsubstituted by independent replacement of one, two, or three or more of the hydrogen atoms thereon with substituents including, but not limited to:

—F, —Cl, —Br, —I,
—OH, protected hydroxy,
—NO$_2$, —CN,
—NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino,
—O—C$_1$-C$_{12}$-alkyl, —O—C$_2$-C$_{12}$-alkenyl, —O—C$_2$-C$_{12}$-alkenyl, —O—C$_3$-C$_{12}$-cycloalkyl, —O-aryl, —O-heteroaryl, —O-heterocycloalkyl,
—C(O)—C$_1$-C$_{12}$-alkyl, —C(O)—C$_2$-C$_{12}$-alkenyl, —C(O)—C$_2$-C$_{12}$-alkenyl, —C(O)—C$_3$-C$_{12}$-cycloalkyl, —C(O)-aryl, —C(O)-heteroaryl, —C(O)-heterocycloalkyl,
—CONH$_2$, —CONH—C$_1$-C$_{12}$-alkyl, —CONH—C$_2$-C$_{12}$-alkenyl, —CONH—C$_2$-C$_{12}$-alkenyl, —CONH—C$_3$-C$_{12}$-cycloalkyl, —CONH-aryl, —CONH-heteroaryl, —CONH-heterocycloalkyl,
—OCO$_2$—C$_1$-C$_{12}$-alkyl, —OCO$_2$—C$_2$-C$_{12}$-alkenyl, —OCO$_2$—C$_2$-C$_{12}$-alkenyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH—C$_2$-C$_{12}$-alkenyl, —OCONH—C$_2$-C$_{12}$-alkenyl, —OCONH—C$_3$-C$_{12}$-cycloalkyl, —OCONH-aryl, —OCONH-heteroaryl, —OCONH-heterocycloalkyl,
—NHC(O)—C$_1$-C$_{12}$-alkyl, —NHC(O)—C$_2$-C$_{12}$-alkenyl, —NHC(O)—C$_2$-C$_{12}$-alkenyl, —NHC(O)—C$_3$-C$_{12}$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkenyl, —NHCO$_2$—C$_3$-C$_{12}$ cycloalkyl, —NHCO$_2$-aryl, —NHCO$_2$-heteroaryl, —NHCO$_2$-heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkenyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkenyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH—C$_1$-C$_{12}$-alkyl, —NHC(NH)NH—C$_2$-C$_{12}$-alkenyl, —NHC(NH)NH—C$_2$-C$_{12}$-alkenyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)—C$_1$-C$_{12}$-alkyl, —NHC(NH)—C$_2$-C$_{12}$-alkenyl, —NHC(NH)—C$_2$-C$_{12}$-alkenyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkenyl, —C(NH)NH—C$_3$-C$_{12}$-cycloalkyl, —C(NH)NH-aryl, —C(NH)NH-heteroaryl, —C(NH)NH— heterocycloalkyl, —S(O)—C$_1$-C$_{12}$-alkyl, —S(O)—C$_2$-C$_{12}$-alkenyl, —S(O)—C$_2$-C$_{12}$-alkenyl, —S(O)—C$_3$-C$_{12}$-cycloalkyl, —S(O)-aryl, —S(O)-heteroaryl, —S(O)-heterocycloalkyl-SO$_2$NH$_2$, —SO$_2$NH—C$_1$-C$_{12}$-alkyl, —SO$_2$NH—C$_2$-C$_{12}$-alkenyl, —SO$_2$NH—C$_2$-C$_{12}$-alkenyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkenyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$CH$_3$, -aryl, -arylalkyl, -heteroaryl, -heteroarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12}$-alkyl, —S—C$_2$-C$_{12}$-alkenyl, —S—C$_2$-C$_{12}$-alkenyl, —S—C$_3$-C$_{12}$-cycloalkyl, —S-aryl, —S-heteroaryl, —S-heterocycloalkyl, or methylthiomethyl.

It is understood that the aryls, heteroaryls, alkyls, and the like can be further substituted.

Compounds of the invention can be prepared according to any suitable method, some of which are known in the art. For example, an acyl phosphonate compound can be prepared by the method of Saady et al. (M. Saady, L. Lebeau, C. Mioskowski, Helv. Chim. Acta 1995, 78, 670-678), using an appropriate alcohol to produce the desired acyl phosphonate compound. One of skill in the art will appreciate the reaction solvent, reaction temperature, and other conditions can be modified to provide the desired compound.

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present invention. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present invention. All crystal forms of the compounds described herein are expressly included in the present invention.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present invention. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds of this invention may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Pharmaceutical Compositions

In another aspect, the invention provides a pharmaceutical composition comprising a compound of the invention, or a pharmaceutically acceptable ester, salt, or prodrug thereof, together with a pharmaceutically acceptable carrier.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur when a compound of the invention is administered with other inhibitors of DXP synthase or other biological (e.g., microbial) targets (e.g., in a cell of a bacterium, parasite, or plant) such as enzymes in the isoprenoid biosynthesis pathway, for example, including enzymes such as DOXP reductase (IspC), 2-C-methyl-D-erythritol 4-phosphate cytidyltransferase (YgbP, IspD), 4-diphosphocytidyl-2-C-methyl-D-erythritol kinase (YchB, IspE), 2-C-methyl-D-erythritol 2,4-cyclodiphosphate synthase (YgbB, IspF), HMB-PP synthase (GcpE, IspG), or HMB-PP reductase (LytB, IspH). In one embodiment, the compound is an inhibitor of IspC such as fosmidomycin. In another embodiment, a compound of the invention can be combined with a compound that reduces efflux of the compound of the invention from the microbial cell (i.e., to increase the effective concentration of the compound of the invention in the microbial cell). Where the compounds of the invention are administered in conjunction with other therapies, dosages of the co-administered compounds will of course vary depending on the type of co-drug employed, on the specific drug employed, on the condition being treated and so forth.

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Methods of Use

In another aspect, the invention provides a method of treating a disease in a subject comprising administering to the subject a compound, pharmaceutically acceptable salt, ester or prodrug of a compound of the invention. In certain embodiments, the disease is a disease related to infection by a bacterium or parasite.

In another aspect, the invention provides a method of inhibiting 1-deoxy-D-xylulose-5-phosphate synthase, the method comprising contacting 1-deoxy-D-xylulose-5-phosphate synthase with a compound or salt of the invention. In certain embodiments, the 1-deoxy-D-xylulose-5-phosphate synthase is contacted with a compound or salt of the invention in vitro or in vivo. In certain embodiments, the 1-deoxy-D-xylulose-5-phosphate synthase is a bacterial 1-deoxy-D-xylulose-5-phosphate synthase.

In certain embodiments, the compound or salt of the invention is at least about 30-fold selective for 1-deoxy-D-xylulose-5-phosphate synthase over a mammalian ThDP-dependent enzyme.

In another aspect, the invention provides a method of inhibiting isoprenoid biosynthesis in a microorganism, the method comprising contacting the microorganism (in vivo or in vitro) with a compound or salt of the invention.

In another aspect, the invention provides a method of inhibiting growth of a bacterial cell (in vivo or in vitro), the method comprising contacting the bacterial cell with a compound or salt of the invention.

In certain embodiments, the subject is administered an additional therapeutic agent.

In a further embodiment, the compound and the additional therapeutic agent are administered simultaneously or sequentially.

In certain embodiments, the invention provides a method wherein the subject is a human.

In another aspect, the invention provides a method of inhibiting growth of a parasite (in vivo or in vitro), the method comprising contacting the parasite with a compound or salt of the invention.

In another aspect, the invention provides a method of inhibiting growth of a plant, the method comprising contacting the plant with a compound or salt of the invention.

In another aspect, the invention provides a method of inhibiting growth of a plant cell (in vivo or in vitro), the method comprising contacting the plant cell with a compound or salt of the invention.

In other embodiments, the invention provides a method wherein the compound of the invention has a Ki for inhibiting DXP synthase less than about 10 micromolar, more preferably less than about 1 micromolar.

As inhibitors of DXP synthase, the compounds and compositions of this invention are particularly useful for treating or lessening the severity of a disease, condition, or disorder where DXP synthase (e.g., of a pathogen such as a bacterium or parasite) is implicated in the disease, condition, or disorder. In one aspect, the present invention provides a method for treating or lessening the severity of a disease, condition, or disorder where DXP synthase is implicated in the disease state (e.g., wherein a bacterium or parasite requires DXP synthase enzymatic activity to grow, reproduce, or exhibit a pathogenic effect). In another aspect, the present invention provides a method for treating or lessening the severity of a disease, condition, or disorder where inhibition of DXP synthase enzymatic activity is implicated in the treatment of the disease. In another aspect, this invention provides a method for treating or lessening the severity of a disease, condition, or disorder with compounds that inhibit enzymatic activity by binding to DXP synthase. Another aspect provides a method for treating or lessening the severity of a disease, condition, or disorder by inhibiting enzymatic activity of DXP synthase with a DXP synthase inhibitor.

The activity of the compounds as DXP synthase inhibitors may be assayed in vitro, in vivo or in a cell line. In vitro assays include assays that determine inhibition of the DXP synthase activity or the growth of a cell (e.g., a bacterium or parasite). Detailed conditions for assaying a compound utilized in this invention as an inhibitor of DXP synthase are set forth in the Examples below.

In accordance with the foregoing, the present invention further provides a method for preventing or treating any of the diseases or disorders described above in a subject in need of such treatment, which method comprises administering to said subject a therapeutically effective amount of a compound of the invention or a pharmaceutically acceptable salt thereof. For any of the above uses, the required dosage will vary depending on the mode of administration, the particular condition to be treated and the effect desired.

According to the methods of treatment of the present invention, disorders are treated or prevented in a subject, such as a human or other animal, by administering to the subject a therapeutically effective amount of a compound of the invention, in such amounts and for such time as is necessary to achieve the desired result. The term "therapeutically effective amount" of a compound of the invention, as used herein, means a sufficient amount of the compound so as to decrease the symptoms of a disorder in a subject. As is well understood in the medical arts a therapeutically effective amount of a compound of this invention will be at a reasonable benefit/risk ratio applicable to any medical treatment.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.01 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

In certain embodiments, a therapeutic amount or dose of the compounds of the present invention may range from about 0.1 mg/Kg to about 500 mg/Kg, alternatively from about 1 to about 50 mg/Kg. In general, treatment regimens according to the present invention comprise administration to a patient in need of such treatment from about 10 mg to about 1000 mg of the compound(s) of this invention per day in single or multiple doses. Therapeutic amounts or doses will also vary depending on route of administration, as well as the possibility of co-usage with other agents.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present invention will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The invention also provides for a pharmaceutical combinations, e.g. a kit, comprising a) a first agent which is a compound of the invention as disclosed herein, in free form or in pharmaceutically acceptable salt form, and optionally b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of the invention and a co-agent, are both administered to a patient simultaneously in the form of a single entity or dosage. The term "non-fixed combination" means that the active ingredients, e.g. a compound of the invention and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

In certain embodiments, these compositions optionally further comprise one or more additional therapeutic agents. For example, antimicrobial or other antibiotic agents may be combined with the compounds of this invention to treat parasitic or microbial infections. Examples of known agents include, but are not limited to, antibiotics that target the ribosome (including the 50S and 30S subunits), cell wall synthesis, DNA gyrase, or DNA topoisomerase, including penicillin and other beta-lactam antibiotics, tetracyclines, anti-malarial compounds such as quinine, mefloquine, chloroquine, artemisinin, and pyrimethamine, treatments for toxoplasmosis such as sulfadiazine, clindamycin, spiramycin, atovaquone, and the like.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The compounds of the invention or pharmaceutical salts thereof may be formulated into pharmaceutical compositions for administration to animals or humans. These pharmaceutical compositions, which comprise an amount of the protein inhibitor effective to treat or prevent a DXP-synthase-mediated condition and a pharmaceutically acceptable carrier, are another embodiment of the present invention.

In another aspect, the invention provides a kit comprising a compound of the invention, and instructions for use in treating a bacterial or parasitic infection.

EXAMPLES

General. Unless otherwise noted, all reagents were obtained from commercial sources. HPLC analyses were performed on a Beckman Gold Nouveau System with a Grace Alltima 3 μm C18 analytical Rocket® column (53 mm×7 mm). Spectrophotometric analyses were carried out on a Beckman DU 800 UV/Vis spectrophotometer. Mass spectrometric analyses were either performed on Shimadzu LC-MS IT-TOF, Thermo Fisher Finnigan LCQ Classic or obtained through the University of Illinois at Urbana-Champaign Mass Spectrometry Lab. All enzymatic reactions were carried out in low-retention microcentrifuge tubes to prevent adsorption of hydrophobic substrates. All enzyme reactions contain 10% DMSO to solubilize hydrophobic substrates. The natural reaction is minimally impacted under these conditions. Purification of recombinant DXP synthase was performed as previously described.[19] For example, $E.$ $coli$ wild-type DXP synthase 1 and $E.$ $coli$ MEP synthase (IspC)2 were overexpressed and purified as reported previously. Protein concentration was determined using the Bradford assay. Porcine pyruvate dehydrogenase was obtained from a commercial source (Sigma Aldrich, St. Louis, Mo., USA) and specificity activity was determined by the manufacturer. For chemical synthesis, dichloromethane was distilled over calcium hydride. Anhydrous acetonitrile was packed in Sure-Seal bottles. All reactions were carried out under an inert argon atmosphere. NMR spectra were taken on a Varian 500 MHz spectrometer. Reaction progress was monitored via $^{31}P$ NMR with triphenylphosphine oxide (TPPO, $\delta=0$ ppm) dissolved in deuterated benzene as an external standard. Chemical shifts are reported in units of parts per million (ppm), relative to a standard reference point. $^1H$ NMR chemical shifts are reported relative to tetramethylsilane (TMS, $\delta=0$ ppm) as internal reference. Preparative HPLC was performed on a Beckman Gold Noveau system with a Varian Dynamax 250×21.4 mm Microsorb C18 column. Antimicrobial data were collected on a Molecular Devices Spectramax Plus 384 plate reader by observing OD600 over time. The $E.$ $coli$ ΔtolC efflux transporter knockout strain (JW5503-1) and parent BW25113 strains were obtained from the Yale Coli Genetic Stock Center (New Haven, Conn., USA). All microbial manipulation of pathogenic bacteria was conducted in a certified biosafety level 2 laboratory with all associated safety protocols.

HPLC Analysis of DXP Synthase-Catalyzed C—N Bond Formation and Product Characterization.

Reaction mixtures containing 100 mM HEPES, pH 8.0, 2 mM MgCl2, 5 mM NaCl, 1 mM ThDP, 1 mg/mL BSA, 10-20 mM pyruvate, 10% DMSO, 0.5 mM 5 mM nitroso substrate were pre-incubated at 37° C. for 5 min. Reactions were initiated with 1-5 .μM enzyme. Aliquots of enzymatic mixture were removed at various time intervals and quenched into an equal volume of cold methanol. Quenched mixtures were incubated on ice for 20 minutes. Precipitated proteins were removed by centrifugation, and the supernatant was analyzed by HPLC with UV detection using the following conditions: Flow rate=3 mL/min; Solvent A: 100 mM NH$_4$OAc, pH 4.6; Solvent B: acetonitrile; Method: 0-100% B over 10 min. New products formed were extracted from the supernatant using ethyl acetate (3×). Combined organic extracts were concentrated, and the resulting samples were dissolved in MeOH and re-subjected to HPLC analysis to confirm that product degradation does not take place during the extraction procedure. Products were subsequently characterized by mass spectrometry.

Determination of Kinetic Parameters for Nitroso Substrates.

Reaction mixtures containing 100 mM HEPES, pH 8.0, 2 mM MgCl$_2$, 5 mM NaCl, 1 mM ThDP, 1 mg/mL BSA, 10-20 mM pyruvate, 10% DMSO v/v, and 10-300 μM nitroso substrate were pre-incubated at 37° C. for 5 min. Enzymatic reactions were initiated by addition of 0.5-2 μM DXP synthase (or 0.1 units/ml PDH) and monitored spectrophotometrically by measuring the rate of disappearance of the nitroso substrate at its corresponding λmax. Substrate concentration as a function of time was determined from absorbance values using Beer's Law. Initial reaction rates were determined from the linear range of the reaction progress curve, usually within 1-3 min. Data analysis to determine kcat and Km for each alternative substrate was carried out using GraFit version 7 from Erithacus Software.

Evaluation of Nitroso Substrates as Inhibitors of DXP Formation.

Reaction mixtures containing 100 mM HEPES, pH 8.0, 2 mM $MgCl_2$, 5 mM NaCl, 1 mM ThDP, 1 mg/mL BSA, 10% DMSO v/v, 30 μM D-GAP, 80 μM pyruvate, and varying concentrations of nitroso inhibitor were pre-incubated at 37° C. for 5 min. Enzyme reactions were initiated by addition of 0.1 μM DXP synthase. Aliquots (150 μL) of the enzymatic mixture were removed between 0.5 and 3 minutes and quenched into ice-cold methanol (150 μL). Precipitated protein was removed by centrifugation, and the supernatant was diluted in an equal volume of water. The nitroso substrate was removed by extraction into acetonitrile (3×), using a previously described freeze-extraction technique.[32] The aqueous layer maintained a constant ratio of D-GAP and DXP during the extraction, and was subjected to derivatization conditions to produce the corresponding hydrazones, using 5-fold excess 2,4-dinitrophenylhydrazine [19] for 20 min to ensure complete derivatization of substrates and product at low concentration. The derivatization mixtures were analyzed by HPLC as previously described.[19] To determine initial reaction rates in the presence of varying inhibitor concentration, the D,L-GAP and DXP hydrazone HPLC peak areas were measured, and the product concentration was determined as a percent of total peak area and plotted against reaction time. Initial rates GraFit version 7 from Erithacus Software was utilized to generate $IC_{50}$ curves.

Active Site Volume Calculations.

Coordinates for ThDP-dependent enzymes, *D. radiodurans* DXS (2O1X), [16] human PDHE1p (3EXE)[33] and transketolase (3MOS)[34] were structurally aligned in Coot [28] using LSQ Superpose and residue ranges A:151-164 (2O1X), E:164-177 (3EXE) and A:152-165 (3MOS). The choice of residues was based on the close proximity to ThDP in order to maximize a similar orientation of the active site region of interest. The r.m.s. deviation, calculated with VMD [35] between residues lining the ThDP binding site was 1.54 Å (2O1X:3EXE) and 1.01 Å (2O1X:3MOS) for 16 Ca backbone atoms. The biological assembly of transketolase (3MOS) was determined using the PISA [36] web-server. Aligned structures were uploaded to the Pocket-Finder [29] web-server to determine active site pocket volumes. Co-factors ThDP or ThDP and metal ions were treated as part of the protein and all other molecules discarded for purposes of defining the protein surface for pocket detection. Pocket-Finder reported volumes and generated space-filling models for the active site pocket in each structure corresponding to the pocket adjacent to TDP in chain A of 2O1X. An overlay of the mesh representations with respect to the active site co-factor and metal ion was rendered in PyMOL (The PyMOL Molecular Graphics System, Version 1.5.0, Schrödinger, LLC).

Active site pocket hydrophobicity calculations using fpocket. Fpocket [30] was run to detect and analyze pockets in DXP synthase (2O1X), PDH (3EXE) and TK (3MOS). The complete coordinate file for DXP synthase and PDH, and the biological assembly for TK, were used as inputs for fpocket. The default cofactor list for fpocket was modified to include TDP and TPP prior to program compilation so that the ThDP cofactor would be treated as a part of the protein as opposed to a removable ligand. The pockets corresponding to the active sites used for the volume calculations using Pocket Finder were determined visually and the parameters recorded.

Inhibition of DXP Synthase by BnAP.

In order to evaluate the inhibitory activity of BnAP against DXP synthase, a continuous spectrophotometric coupled assay was used to measure formation of DXP by monitoring IspC consumption of NADPH (340 nm). [2] DXP synthase reaction mixtures (previously described) including BnAP (15, 30, and 60 μM), IspC (1 μM) and NADPH (100 μM) were pre-incubated at 37° C. for 5 minutes. Initial rates were measured after the reaction was initiated by the addition of DXP synthase. Inhibition of the coupling enzyme (IspC) by BnAP was not observed up to 1.5 mM. Experiments were performed in triplicate. Double reciprocal analysis of data was carried out using GraFit version 7 from Erithacus Software.

Inhibition of PDH by BnAP.

Pyruvate dehydrogenase activity was measured spectrophotometrically as previously reported [38] by monitoring absorbance changes at 340 nm due to reduction of $NAD^+$ by PDH. Reaction mixtures contained 100 mM HEPES (pH 8.0), 1 mg/mL BSA, 0.2 mM ThDP, 0.1 mM coenzyme A, 1 mM $MgCl_2$, 2 mM cysteine, 0.3 mM tris(2-carboxyethyl)phosphine (TCEP). The reaction was initiated with enzyme (0.01 units/ml) and activity was monitored at 30° C. For inhibition studies, reaction mixtures (described above) including BnAP (0.5, 1, 2.25 mM) were pre-incubated at 30° C. for 5 minutes. Initial rates were measured immediately after reactions were initiated by addition of PDH (0.01 units/ml). Double reciprocal analysis of data was carried out using GraFit version 7 from Erithacus Software.

Synthesis of BnAP (Scheme 1).

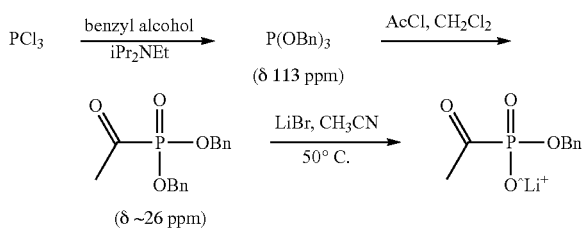

Scheme 1. Synthesis of BnAP.

Benzylacetylphosphonate was prepared from phosphorus trichloride using standard procedures. Tribenzyl phosphite was generated from benzyl alcohol, diisopropylethylamine and phosphorous trichloride according to Saady et al. [37] The spectral properties of the compound are identical to published values. For the preparation of benzylacetylphosphonate (BnAP), a flame-dried flask, cooled under argon, was charged with 0.32 mL (4.5 mmol) acetyl chloride. Tribenzyl phosphite (0.46 g, 1.3 mmol) was dissolved in 13 mL of anhydrous dichloromethane, and the resulting mixture was added dropwise to acetyl chloride. Reaction progress was monitored via 31P NMR, and complete conversion of tribenzyl phosphite (δ 113 ppm) to dibenzylacetylphosphonate (δ −26 ppm) was observed within one hour. Volatiles were removed in vacuo, and the crude material was used without further purification.

Dibenzylacetylphosphonate was dissolved in 2.2 mL of anhydrous acetonitrile, and lithium bromide (0.17 g, 0.95 mmol) was added in one portion. The reaction mixture was heated to 50° C. for ~4 hours. The lithium salt of benzylacetylphosphonate precipitated from solution and was removed by filtration. The filter cake was washed successively with 20 mL portions of cold acetonitrile and diethyl ether. The crude product was purified by reversed-phase preparative HPLC. Flow rate=10 mL/min; Solvent A: 50 mM HNEt$_3$OAc, pH 6.0; Solvent B: Methanol; Method 5-80% B over 75 minutes. The purity of fractions was determined by analytical reverse-phase HPLC. Flow rate=3 mL/mM; Solvent A: 50 mM HNEt$_3$OAc, pH 6.0; Solvent B: Methanol; Method 5-80% B over 12 minutes. Combined fractions were lyophilized to yield a final mass of 0.0975 grams BnAP as the triethylammonium salt (24% over two steps). $^{31}$P NMR (D$_2$O): δ −27.43 (s) $^1$H-NMR (D$_2$O): δ 1.20 (t, 9H), 2.31 (d, 3H), 3.11 (m, 6H), 4.91 (d, 2H), 7.35 (m, 5H). HRMS (ESI), calculated m/z for C$_{15}$H$_{27}$NO$_4$P (triethylammonium salt), [M+H]+=316.1678; observed: 316.1673.

Synthesis of Alkyl Acetylphosphonates

Trialkyl phosphites, acyl chloride and lithium bromide were obtained from commercial sources and used without further purification. Methylene chloride and acetonitrile were distilled over calcium hydride and collected under an argon atmosphere. All reactions were carried out in flame-dried glassware under an inert argon atmosphere. NMR spectra were recorded on a Varian 500 MHz spectrophotometer and processed via the ACD/NMR Processor Academic Edition. Chemical shifts are reported in units of parts per million (ppm), relative to a standard reference. $^1$H NMR chemical shifts are reported relative to the residual $^1$H signal of the deuterated solvent as an internal reference (CDCl$_3$ δ=7.27 ppm; D$_2$O δ=4.75 ppm). $^{31}$P chemical shifts are reported relative to triphenylphosphine oxide (TPPO, δ=0 ppm) as an external standard. Mass spectrometry analysis was carried out at the University of Illinois at Urbana-Champagne, School of Chemical Sciences, Mass Spectrometry Laboratory. BAP and BnAP were synthesized as reported previously [18], [39].

Scheme 2. Synthesis of PentAP, HexAP, OctAP and iPrAP.

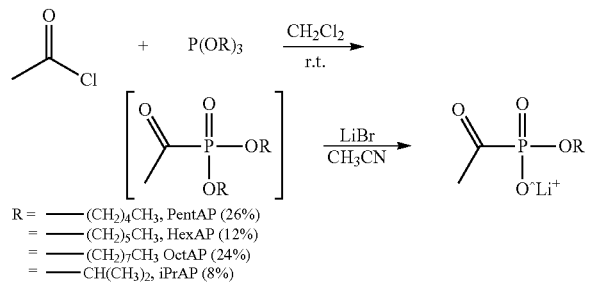

R = —(CH$_2$)$_4$CH$_3$, PentAP (26%)
  = —(CH$_2$)$_5$CH$_3$, HexAP (12%)
  = —(CH$_2$)$_7$CH$_3$ OctAP (24%)
  = —CH(CH$_3$)$_2$, iPrAP (8%)

Synthesis of Pentylacetylphosphonate (PentAP): A flame-dried flask, cooled under argon, was charged with acetyl chloride (0.7 mL, 10 mmol). Tripentyl phosphite (0.98 g, 3.4 mmol) was dissolved in anhydrous CH$_2$Cl$_2$ (32 mL), and the resulting solution was added drop-wise to the stirring acetyl chloride. Following addition of the trialkyl phosphite, argon was bubbled through the reaction mixture to remove HCl byproduct. The progress of the reaction was monitored by $^{31}$P NMR spectroscopy, and the complete conversion of tripentyl phosphite (δ=113 ppm) to dipentylacetylphosphonate (δ=−28 ppm) was observed within 1 h. Volatiles were removed in vacuo, and the crude material was used without further purification. Dipentylacetylphosphonate was dissolved in anhydrous acetonitrile (5.6 mL), and lithium bromide (0.38 g, 4.4 mmol) was added in one portion. The reaction mixture was heated to 65° C. and stirred overnight. The lithium salt of pentylacetylphosphonate precipitated from solution and was removed by filtration. The filter cake was washed successively with cold acetonitrile, diethyl ether and methylene chloride (30 mL portions of). Lithium pentylacetylphosphonate was isolated as a white powder (177 mg, 26% yield). $^1$H NMR (D$_2$O): δ=0.81 ppm (t, 3H), 1.26 ppm (m, 4H), 1.53 ppm (m, 2H), 2.37 ppm (d, 3H), 3.82 ppm (m, 2H); $^{31}$P NMR (D$_2$O): δ=−27.6 ppm (s); HRMS (ESI): m/z calcd for C$_7$H$_{16}$O$_4$P (H+ form): 195.0786 [M+H]+, found: 195.0788.

Synthesis of Hexylacetylphosphonate (HexAP): A flame-dried flask, cooled under argon, was charged with acetyl chloride (1.1 mL, 15 mmol). Trihexyl phosphite (1.68 g, 5.0 mmol) was dissolved in anhydrous CH$_2$Cl$_2$ (50 mL), and the resulting solution was added drop-wise to the stirring acetyl chloride. Following addition of the trialkyl phosphite, argon gas was bubbled through the reaction mixture to remove HCl byproduct. The progress of the reaction was monitored by $^{31}$P NMR spectroscopy, and the complete conversion of trihexyl phosphite (δ=117 ppm) to dihexylacetylphosphonate (δ=−28 ppm) was observed within 2 h. Volatiles were removed in vacuo, and the crude material was used without further purification. Dihexylacetylphosphonate was dissolved in anhydrous acetonitrile (8.3 mL), and lithium bromide (0.65 g, 7.5 mmol) was added in one portion. The reaction mixture was heated to 65° C. and stirred overnight. The lithium salt of hexylacetylphosphonate precipitated from solution and was removed by filtration. The filter cake was washed successively with cold acetonitrile, diethyl ether and methylene chloride (30 mL portions). Lithium hexylacetylphosphonate was isolated as a white solid (130 mg, 12% yield over two steps). $^1$H NMR (D$_2$O): δ=0.77 ppm (t, 3H), 1.20 ppm (m, 6H), 1.56 ppm (m, 2H), 2.35 ppm (d, 3H), 3.83 ppm (m, 2H); $^{31}$P NMR (D$_2$O): δ=−27.6 ppm (s); HRMS (ESI): m/z calcd for C$_8$H$_{18}$O$_4$P (H+ form): 209.0943 [M+H]+, found: 209.0944.

Synthesis of Octylacetylphosphonate (OctAP): A flame-dried flask, cooled under argon, was charged with acetyl chloride (1.1 mL, 15 mmol). Trioctyl phosphite (2.1 g, 5.0 mmol) was dissolved in anhydrous CH$_2$Cl$_2$ (50 mL), and the resulting solution was added drop-wise to the acetyl chloride. Following addition of the trialkyl phosphite, argon was bubbled through the reaction mixture. The progress of the reaction was monitored via $^{31}$P NMR spectroscopy, and the complete conversion of trioctyl phosphite (δ=ppm) to dioctylacetylphosphonate (δ=−28 ppm) was observed within 1 h. Volatiles were removed in vacuo, and the crude material was used without further purification. Dioctylacetylphosphonate was dissolved in anhydrous acetonitrile (8.3 mL), and lithium bromide (0.65 g, 7.5 mmol) was added in one portion. The reaction was heated to 60° C. and stirred overnight. The lithium salt of octylacetylphosphonate precipitated from solution and was removed by filtration. The filter cake was washed successively with cold acetonitrile and diethyl ether (30 mL portions of). Lithium octylacetylphosphonate was isolated as a white powder (290 mg, 24% over two steps). $^1$H NMR (D$_2$O): δ=0.7 ppm (m 7H), 0.93 ppm (m, 2H), 1.2 ppm (m, 4H), 1.5 ppm (m, 2H), 2.36 ppm (d, 3H), 3.85 ppm (m, 2H); $^{31}$P NMR (D$_2$O): δ=−27.7 ppm (s); HRMS (ESI): m/z calcd for C$_{10}$H$_{22}$O$_4$P (H+ form): 237.1256 [M+H]+, found: 237.1255.

Synthesis of Isopropylacetylphosphonate (iPrAP): A flame-dried flask, cooled under argon, was charged with acetyl chloride (0.3 mL, 4 mmol). Triisopropyl phosphite (0.9 mL, 4 mmol) was added neat to the acetyl chloride. The progress of the reaction was monitored via $^{31}$P NMR spectroscopy, and the complete conversion of the trialkyl phosphite (δ=113 ppm) to diisopropylacetylphosphonate (δ=−27 ppm) was observed within 1 h. The product was purified by vacuum distillation and isolated as a pale yellow oil (471 mg, 59% yield). Diisopropylacetylphosphonate was dissolved in anhydrous acetonitrile (2.8 mL), and lithium bromide (0.18 g, 2.0 mmol) was added in one portion. The reaction was heated to 70° C. and stirred overnight. The lithium salt of isopropylacetylphosphonate precipitated from solution and was removed by filtration. The filter cake was washed successively with cold acetonitrile and diethyl ether (15 mL portions of). Lithium isopropylacetylphosphonate was isolated as a white powder (57 mg, 15% yield). $^1$H NMR (D$_2$O) 1.21 ppm (d, 6H), 2.37 ppm (d, $^3$H), 4.36 ppm (m, 1H); $^{31}$P NMR (D$_2$O): δ=−28.3 ppm (s); HRMS (ESI): m/z calcd for C$_5$H$_{12}$O$_4$P (H$^+$ form): 167.0473 [M+H]$^+$, found: 167.0469.

Aromatic Aldehydes as DXP Synthase Substrates.

Some ThDP-dependent enzymes are known to catalyze C—C bond formation using aromatic substrates with varying turnover efficiencies; [20] [21] [22] however, there are no reports describing DXP synthase usage of aromatic substrates. As a starting point, we tested several aromatic aldehydes as acceptor substrates. 2-Hydroxy-4,6-dinitrobenzaldehyde appeared to be amongst the best of those tested, and was therefore fully characterized as a substrate for DXP synthase. In this case, the K$_m$ is 512+/−20 μM, ~18-fold higher than the natural substrate, D-GAP, and the k$_{cat}$ is low (k$_{cat}$=0.35+/−0.05 min$^{-1}$). The aromatic aldehyde study suggested that there may be flexibility in the active site of DXP synthase toward aromatic acceptor substrates (data not shown). However, a significant number of aromatic aldehydes are not turned over by DXP synthase, suggesting the low intrinsic reactivity of aromatic aldehydes as a limiting factor in substrate specificity studies to probe the enzyme active site.

DXP Synthase-Catalyzed C—N Bond Formation

The nitroso group is a functional isostere of the aldehyde group and is known to possess higher reactivity toward nucleophiles. In fact, ThDP-utilizing enzymes transketolase (TK), pyruvate decarboxylase (PDC), benzaldehyde lyase (BAL) and pyruvate dehydrogenase (PDH) have been shown to use aromatic nitroso analogs as acceptor substrates in the formation of hydroxamic acids. [23] [24] [25] [26] [27a,b] We hypothesized that a substrate specificity study of DXP synthase using the intrinsically more reactive aromatic nitroso compound class would better inform us about key binding elements of aromatic substrates. In addition, we postulated that such a study could reveal a new application of DXP synthase as a biocatalyst for the generation of the medicinally-important hydroxamic acid class.

Thus, a series of aromatic nitroso analogs was tested as substrates for DXP synthase (FIG. 2).

Notably, DXP synthase turns over a range of structurally diverse nitroso substrates (1, 3-9, FIG. 2); most aldehyde counterparts for the nitroso analogs tested are not substrates for the enzyme, consistent with the idea that the nitroso isostere is more reactive. A single C-nitroso analog 10 did not act as substrate for the enzyme. Similarly, N-nitroso compounds are not substrates. The electron rich p-dimethylamino nitroso analog 4 is a substrate for the enzyme, whereas it is not a substrate for yeast TK. [26] Interestingly, the corresponding amides, presumably produced via a mechanism involving the unstable hydroxamic acid as an intermediate, [25] were detected as the major products of several electron rich substrates (4-8). This result has been reported in the study that examined the turnover of 4 by PDC. [25] However, the observation that the amide is also isolated from naphthol substrates was unexpected. In order to rule out the possibility that BSA added to enzymatic reaction mixtures catalyzes formation of amide products, control reactions were performed on 4 and 5 in the absence of BSA. In both cases, only the corresponding amides were detected.

Kinetic parameters were measured spectrophotometrically for the alternative substrates shown in Table 1.

TABLE 1

Substrate specificity of nitroso substrates.[a]

| Substrate | k$_{cat}$ [min$^{-1}$][b] | K$_m$ [μM][b] | k$_{cat}$/K$_m$ (×10$^4$) [M$^{-1}$ min$^{-1}$] |
|---|---|---|---|
| D-GAP | 102 ± 7 | 28 ± 4 | 364 ± 60 |
| 1 | 175 ± 19 | 133 ± 18 | 132 ± 20 |
| 3 | 36 ± 7 | 99 ± 16 | 36 ± 9 |
| 4 | 0.9 ± 0.1 | 54 ± 13 | 1.7 ± 0.5 |
| 5 | 1.1 ± 0.2 | 41 ± 10 | 2.7 ± 0.8 |
| 6 | 2.0 ± 0.2 | 24 ± 6 | 8 ± 2 |
| 7 | 1.18 ± 0.04 | 18 ± 4 | 6.6 ± 1.5 |
| 8 | 1.3 ± 0.2 | 63 ± 7 | 2.1 ± 0.4 |
| 9 | 1.4 ± 0.2 | 387 ± 18 | 0.36 ± 0.05 |

[a]Reaction conditions: 100 mM HEPES, pH 8.0, 2 mM MgCl$_2$, 5 mM NaCl, 1 mM ThDP, 1 mgmL$^{-1}$ BSA, 10-20 mM pyruvate, 10% DMSO (v/v), 37° C.
[b]Performed in triplicate. Values shown are the average ± SEM.

Initially, specificity constants (k$_{cat}$/K$_m$) were measured, revealing a k$_{cat}$/K$_m$ for nitrosobenzene that is comparable to the natural acceptor substrate, D-GAP. Reduced specificity constants were measured for larger naphthol-containing substrates (5-8, Table 1), an observation that is consistent with the idea that sterically demanding naphthol substrates could exhibit a reduction in efficiency of turnover as a consequence of reduced affinity for the enzyme. However, detailed kinetic analysis of nitroso substrate turnover suggests this is not the case. Small nitrosobenzene analogs display higher reactivity (high k$_{cat}$) but lower affinity (higher K$_m$) relative to D-GAP (1 and 3, Table 1). Contrary to our expectations, several sterically demanding alternative substrates exhibit high affinities for DXP synthase, with nitrosonaphthols 5-8 showing comparable affinity to the natural substrate. In these cases, a reduced k$_{cat}$ accounts for lower turnover efficiency, in line with previous reports on the sensitivity of nitroso turnover to substituent effects. [26] The remarkably high affinities measured for sterically demanding substrates on DXP synthase is in stark contrast to previously reported trends in nitroso turnover by ThDP-dependent enzymes, [27] where increasing steric bulk of the substrate correlates with decreased affinity.

Aromatic Nitroso Substrates Exhibit Low Affinity for a Smaller PDH Active Site.

As a basis for selective inhibitor design, we sought to determine whether DXP synthase displays higher affinity for sterically demanding substrates relative to pyruvate dehydrogenase (PDH). Thus, nitroso analogs 1, 4 and 6 were evaluated as substrates for porcine PDH. Our results indicate these aromatic substrates exhibit significantly lower affinities for PDH compared to DXP synthase (Table 2) in contrast to the trend observed for DXP synthase.

TABLE 2

Determination of $K_m$ for nitroso substrates against E. coli DXP synthase (DXPS) compared to the porcine PDH E1 subunit.

| Substrate | PDH $K_m$ [μM][a] | $K_m^{PDH}/K_m^{DXPS}$ |
|---|---|---|
| 1 | 350 ± 30 | 2.7 |
| 4 | 408 ± 60 | 7.5 |
| 6 | 450 ± 16 | 19.3 |

[a]Reaction conditions: 100 mM HEPES, pH 8.0, 2 mM $MgCl_2$, 5 mM NaCl, 1 mM ThDP, 1 mgmL$^{-1}$ BSA, 10-20 mM pyruvate, 10% DMSO (v/v), 37° C. Performed in triplicate; values shown are the average ± SEM.

Nitrosobenzene displays a 2.7-fold increase in $K_m$ for PDH compared to DXP synthase, whereas the largest of the nitroso substrates tested, nitrosonaphthol 6, displays ~19-fold increase in $K_m$ for PDH compared to DXP synthase. We hypothesized the DXP synthase active site may be comparatively larger to accommodate ternary complex formation during catalysis. Indeed, a comparison of active site volumes (calculated by crystal structure coordinates that were aligned in Coot [28] and then analyzed using Pocket-Finder [29]) suggests the DXP synthase active site is significantly larger than the ThDP-dependent enzymes, PDH or transketolase. The hydrophobic nature of alternative nitroso substrates tested could potentially drive selectivity of turnover by DXP synthase. However, when the active site pockets of DXP synthase, PDH and TK were analyzed using fpocket, [30] the computed hydrophobicity score (based on the hydrophobicity scale published by Monera et al.)[31] indicates that the PDH pocket is more hydrophobic than DXP synthase, while TK has the least hydrophobic pocket. Taken together, these results suggest that incorporation of sterically demanding fragments into inhibitor scaffolds may drive selective inhibition and is facilitated mostly by the larger cavity of DXP synthase.

Inhibition of DXP Formation by Nitroso Alternative Substrates

The low $K_m$ values measured for aromatic nitroso substrates suggest these analogs bind with reasonable affinity in the enzyme active site. Thus, we hypothesized that alternative substrates bearing aromatic scaffolds could also act as inhibitors of the natural reaction. Compounds 1 and 3-9 were evaluated as inhibitors of DXP synthase using an HPLC-based assay previously reported.[18] Interestingly, all nitroso compounds exhibited weak inhibitory activity with $IC_{50}$ values ranging from 208 μM to >2 mM and with no apparent trend with measured $K_m$ values (Table 3). As one of the higher affinity substrates, the readily available nitrosonaphthol 5 was selected for further evaluation in an effort to understand the mechanism of inhibition. This inhibitor was found to exhibit a competitive inhibition pattern with respect to D-GAP (apparent $K_i$=422 μM±80 μM.

TABLE 3

Inhibition of DXP formation by nitroso substrates.[a]

| Substrate | $IC_{50}$ [μM][b] |
|---|---|
| 1 | 208 ± 20 |
| 3 | 291 ± 11 |
| 4 | 844 ± 170 |
| 5 | 1065 ± 190 |
|   | ($K_i$ = (422 ± 80) μM) |
| 6 | 522 ± 60 |
| 7 | 354 ± 90 |
| 8 | >2000 |
| 9 | >2000 |

[a]Reaction conditions; 100 mM HEPES, pH 8.0, 2 mM $MgCl_2$, 5 mM NaCl, 1 mM ThDP, 1 mg mL$^{-1}$ BSA, 10% DMSO (v/v), 30 μM D-GAP, 80 μM pyruvate, 37° C.
[b]Performed in triplicate; values shown are the average ± SEM.

The >10-fold difference between the $K_m$ (41±10 μM) and $K_i$ suggests that nitrosonaphthols could adopt a binding mode for turnover that is distinct from the binding mode for inhibition. Alternatively, $K_i$ may reflect the affinity of the Michaelis-Menten complex between enzyme and nitrosonaphthol, whereas the $K_m$ for this substrate may be indicative of a higher affinity ternary complex further along the reaction coordinate in this two substrate system.

Nitrosonaphthols and D-GAP Adopt Distinct Binding Modes During Turnover

R478 and R420 are known to be essential for binding of D-GAP, presumably by anchoring the phosphate group (results to be published elsewhere). Two DXP synthase variants (R478A and R420A) were evaluated as catalysts for C—N bond formation using nitrosonaphthols 5-7. While both of these variants adversely affect the binding of D-GAP, they have no apparent effect on the affinities of nitroso substrates in C—N bond formation, as indicated by comparable $K_m$ values measured for nitroso substrates by both variants and wild type enzyme. This is consistent with the notion that nitrosonaphthols adopt a binding mode for turnover that is distinct from D-GAP.

Selective Inhibition of DXP Synthase by Benzyl Acetylphosphonate (BnAP).

Our results suggest that the comparatively large active site of DXP synthase can accommodate sterically demanding scaffolds, but in a manner that does not interfere with DXP formation. On this basis, we hypothesized that aromatic components could be incorporated into unnatural bisubstrate analogs to impart selectivity of inhibition against DXP synthase. To demonstrate this concept, we prepared benzyl acetylphosphonate (BnAP) as a potential selective inhibitor of DXP synthase. BnAP (Compound 1) incorporates the acetyl phosphonate moiety as a pyruvate mimic and a benzyl group to mimic the alternative acceptor substrate, nitrosobenzene. As expected, BnAP is a competitive inhibitor with respect to pyruvate with reasonable potency against DXP synthase ($K_i$=10.4±1.3 μM), and exhibits ~85-fold higher inhibitory activity against DXP synthase compared to PDH. Additionally, BnAP exhibits an uncompetitive inhibition pattern with respect to D-GAP ($K_i$=70±8 μM). The requirement for D-GAP binding is consistent with the idea that aromatic scaffolds adopt a binding mode that is distinct from D-GAP.

Additional inhibition data for acetyl phosphonate compounds is shown in Table 4:

TABLE 4

| Compound | MW | In vitro DXP syn $IC_{50}$, μM | In vitro DXP syn $K_i$, μM |
|---|---|---|---|
| 1 | 220.09 |  | 10.4 |
| 2 | 246.13 | 64.5 |  |
| 3 | 250.11 | 37.4 |  |
| 4 | 264.14 | 194 |  |
| 5 | 284.18 | 77 | 55 |
| 12 | 170.03 | 20 |  |

Linear Alkyl Acetylphosphonates Inhibit DXP Synthase.

We have shown that pathogenic DXP synthase enzymes are inhibited by the sterically demanding acetylphosphonates, BAP and BnAP, and these are more potent inhibitors of DXP synthase than the related ThDP-dependent enzyme, pyruvate dehydrogenase E1 subunit (PDH) (FIG. 1B). We theorized selectivity could be achieved as a result of the comparatively large active site of DXP synthase and its unique mechanism requiring ternary complex formation during catalysis. Isopropylacetylphosphonate (iPrAP), pentylacetylphosphonate (PentAP), hexylacetylphosphonate (HexAP) and octylacetylphosphonate (OctAP) were synthesized (Scheme 2), and evaluated as inhibitors of *E. coli* DXP synthase. $K_i$ values (Table 5) for PentAP, HexAP and OctAP against DXP synthase are in the low micromolar range and comparable to BAP and BnAP ($K_i^{PentAP}$=9.9±0.4 μM, $K_i^{HexAP}$=8.9±0.5 μM & $K_i^{OctAP}$=6.0±0.2 μM).

TABLE 5

| cpd | $K_i^{DXPS}$ | $K_i^{PDH}$ | $K_i^{PDH}/K_i^{DXPS}$ |
|---|---|---|---|
| BAP[7] | 5.6 ± 0.8 | 335 ± 8 | 60 |
| BnAP[2] | 10 ± 1 | 880 ± 78 | 88 |
| PentAP | 9.9 ± 0.4 | 250 ± 31 | 25 |
| HexAP | 8.9 ± 0.5 | 117 ± 9 | 13 |
| OctAP | 6.0 ± 0.2 | 154 ± 14 | 26 |

Figure 4A:
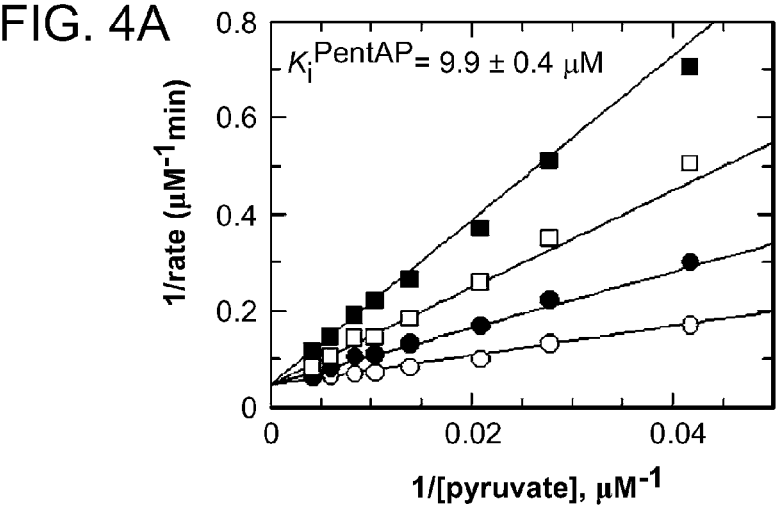
FIG. 4A, FIG. 4B, and FIG. 4C are charts showing competitive inhibition of DXP synthase by pentylacetylphosphonate (PentAP.
Figure 4B:
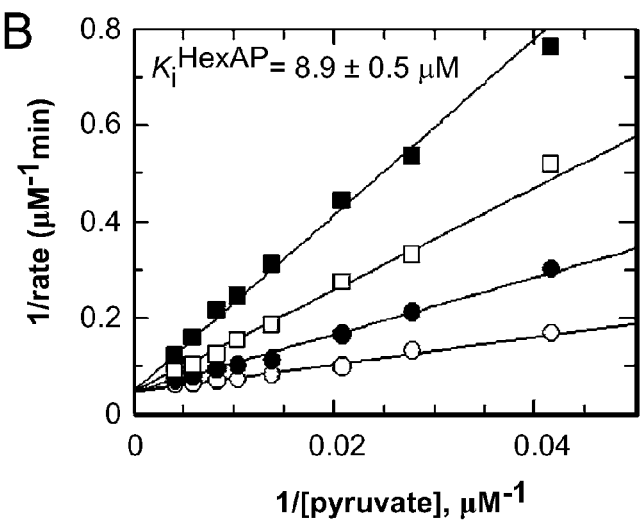
Figure 4C:
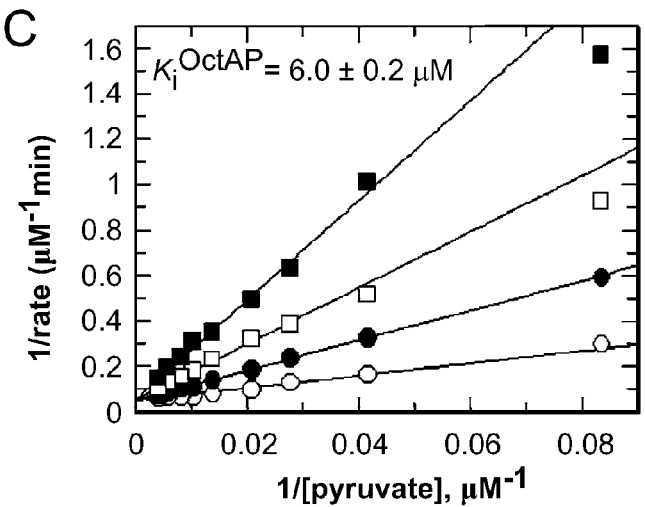
Figure 5:
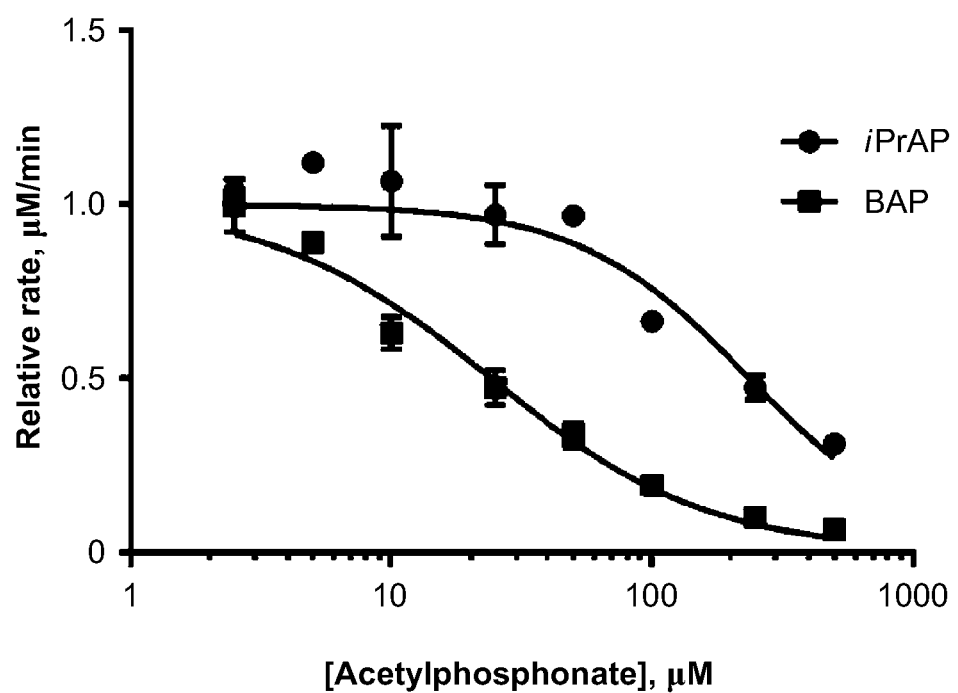
FIG. 5 is a chart showing that isopropylacetylphosphonate (iPrAP) is a weak inhibitor of DXP synthase. Inhibition of DXP synthase was measured as previously described[13, 18]. $IC_{50}$ determinations for BAP (■) and iPrAP (●) were carried out in the presence of pyruvate (95 μM) and D-GAP (56 μM). Acetylphosphonate concentration was varied from 0 to 250 μM. $IC_{50}^{BAP}=24\pm4$ μM, $IC_{50}^{iPrAP}=245\pm67$ μM (GraphPad Prism, error represents 95% Confidence Interval). Experiments were performed in triplicate for BAP and in duplicate for iPrAP

PentAP, HexAP and OctAP display a competitive mode of inhibition with respect to pyruvate (FIG. 4). In contrast, isopropylacetylphosphonate (iPrAP) exhibits weak inhibition of DXP synthase with an $IC_{50}$ an order of magnitude higher than that of BAP ($IC_{50}^{iPrAP}$=250±70 μM; $IC_{50}^{BAP}$=24±4 μM, FIG. 5). Thus, while acetylphosphonates bearing long alkyl chains are readily accommodated in the DXP synthase active site, analogs bearing branched alkyl groups adjacent to the acetylphosphonate moiety exhibit lower affinity for DXP synthase, presumably as a result of unfavorable steric interactions near the cofactor binding site.
Selectivity of DXP Synthase Inhibition Decreases with Increasing Alkyl Chain Length.

Figure 6A:
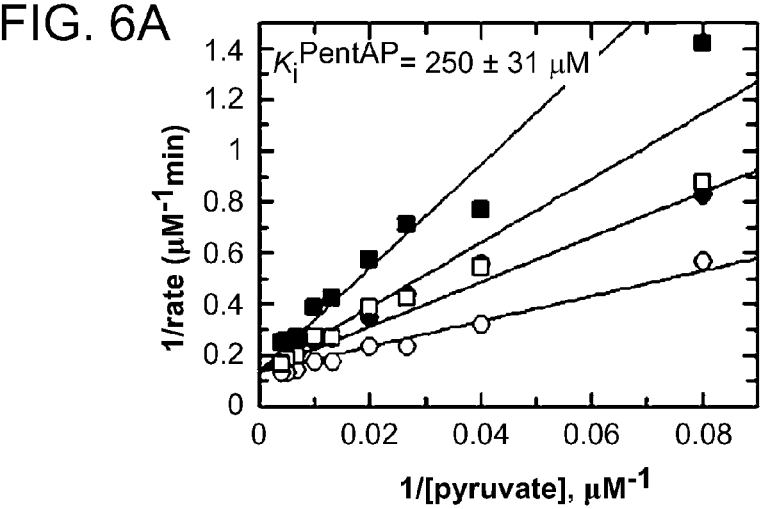
FIG. 6A, FIG. 6B, and FIG. 6C are charts showing Competitive inhibition of procine PDH E1 subunit by PentAP (FIG. 6A), HexAP (FIG. 6B) and OctAP (FIG. 6C). Inhibition assays were performed as previously described[18]. Pyruvate concentration was varied from 12.5-250 μM and acetylphosphonate concentration was varied: 0 μM (○), 250 μM (PentAP) or 200 μM (HexAP and OctAP) (●), 500 μM (□) and 1000 μM (■). Experiments were performed in triplicate, and data were subjected to non-linear regression analysis for $K_i$ determinations (GraphPad Prism). Representative Lineweaver-Burk plots (GraFit from Erithacus Software) are shown for PentAP (FIG. 6A), HexAP (FIG. 6B) and OctAP (FIG. 6B) to illustrate the competitive inhibition mode with respect to pyruvate.
Figure 6B:
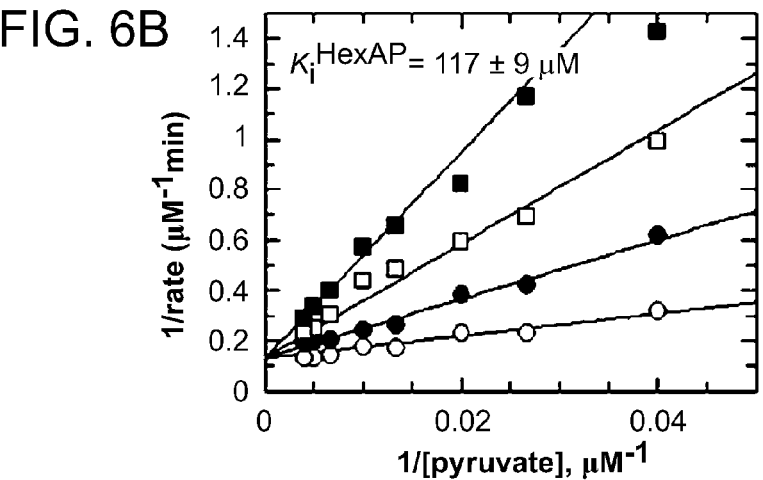
Figure 6C:
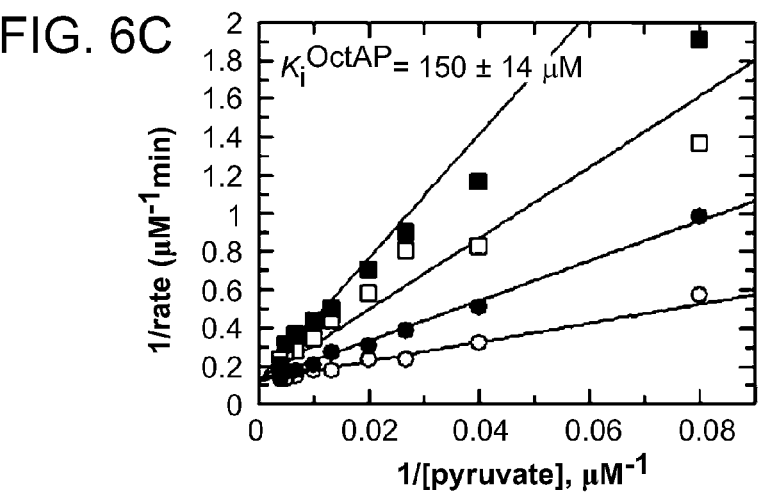
Figures 7A, 7B:
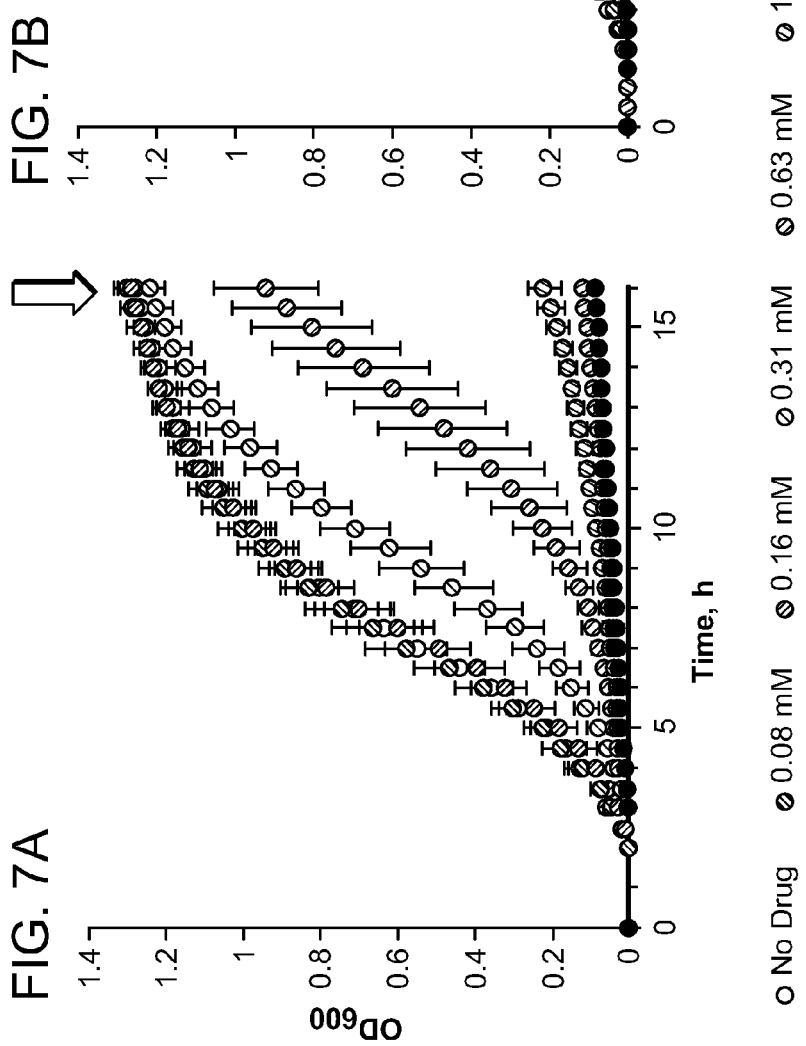
FIG. 7A and FIG. 7B are charts showing representative growth curves are shown for BAP (FIG. 7A) and BnAP (FIG. 7B). Alkylacetylphosphonates exert dose-dependent delay in E. coli K-12 (MG 1655) growth in CAMHB. Fractional growth (measured at 16 h, blue arrow) was determined relative to the no drug control. Standardized cell cultures were exposed to increasing concentrations of acetylphosphonate, and growth was determined by measuring the $OD_{600}$ for a period of 16 hours. Acetylphosphonate concentration was varied from 0-5 mM: No drug (light blue), 0.08 mM (orange), 0.16 mM (gray), 0.31 mM (yellow), 0.63 mM (blue), 1.25 mM (green), 2.5 mM (dark blue) and 5.0 mM (brown).
Figure 8:
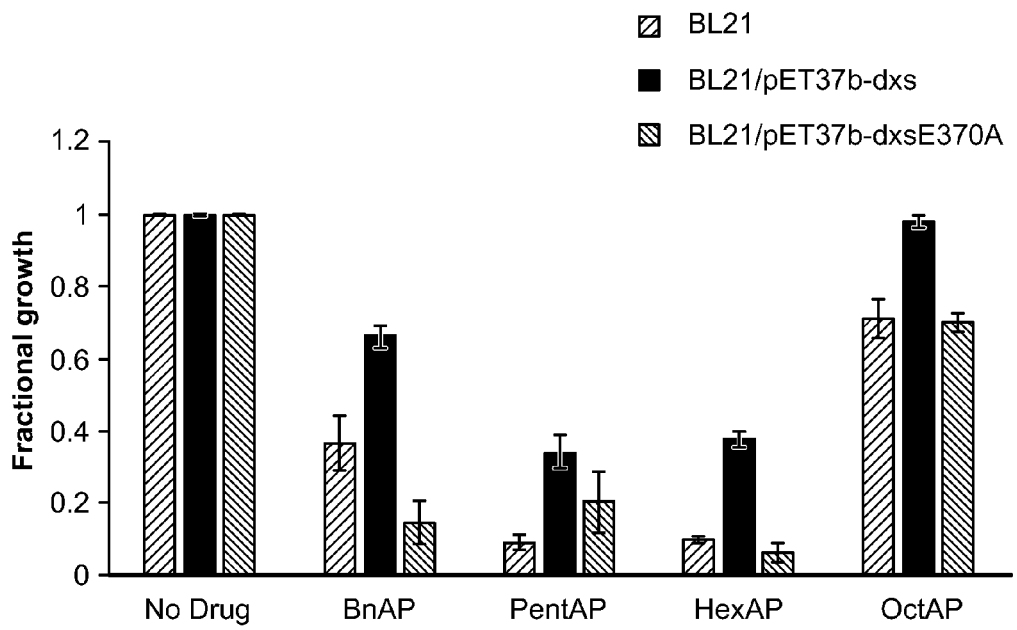
FIG. 8 is a chart showing that increasing intracellular DXP synthase levels results in partial rescue of E. coli growth in the presence of alkylacetylphosphonates. Rescue is observed in the presence of BnAP (0.16 mM), PentAP (0.31 mM), HexAP (0.63 mM) and to some extent OctAP (5 mM). An overnight starter culture of the appropriate cell line was started by inoculating sterile CAMHB with 1 colony. After growing to saturation, the culture was diluted 1:100 into fresh CAMHB and grown to an $OD_{600}$~0.45 (approximately 500 CFU mL$^{-1}$). Cultures were then diluted 1:1 with acetylphosphonate at the indicated concentration, and cultures were grown for 16 hours. Fractional growth (measured at 16 h) was determined relative to the no drug control in each case.
Figure 9:
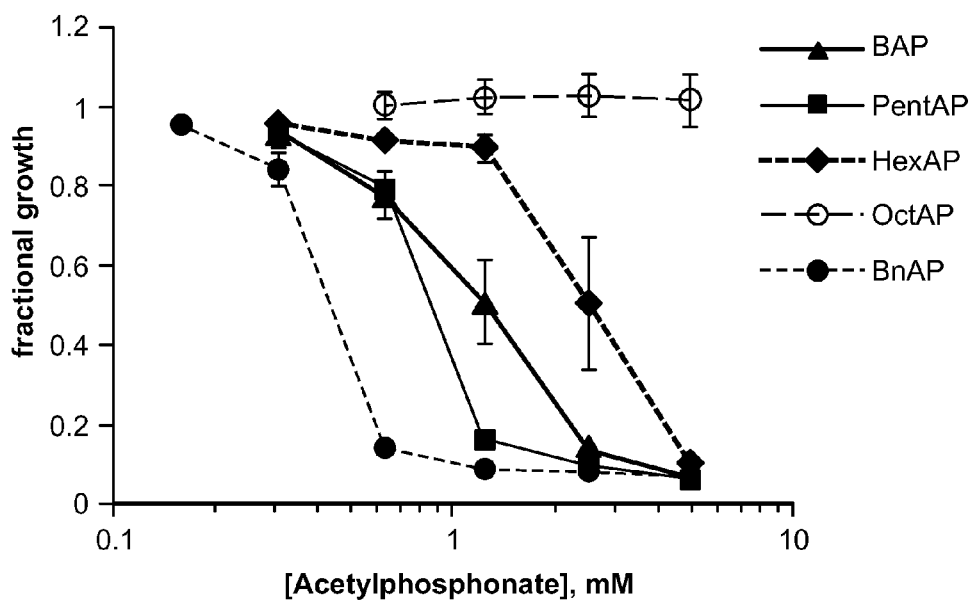
FIG. 9 is a chart showing antimicrobial activity of acetylphosphonates against E. coli BW25113 grown in CAMHB. Standardized cell cultures (approximately ~10$^5$ CFU mL$^{-1}$) were exposed to increasing concentrations of acetylphosphonate. Fractional growth was determined at 16 hours as a percentage of the growth of no drug control. BAP (●), PentAP (■) and HexAP (▲) were varied from 0.31 to 5 mM. OctAP (▼) was varied from 0.63 to 5 mM, and BnAP (♦) was varied from 0.16 mM to 5 mM. Each data point is the average of 3 independent experiments and the error bars are standard error.
Figure 10:
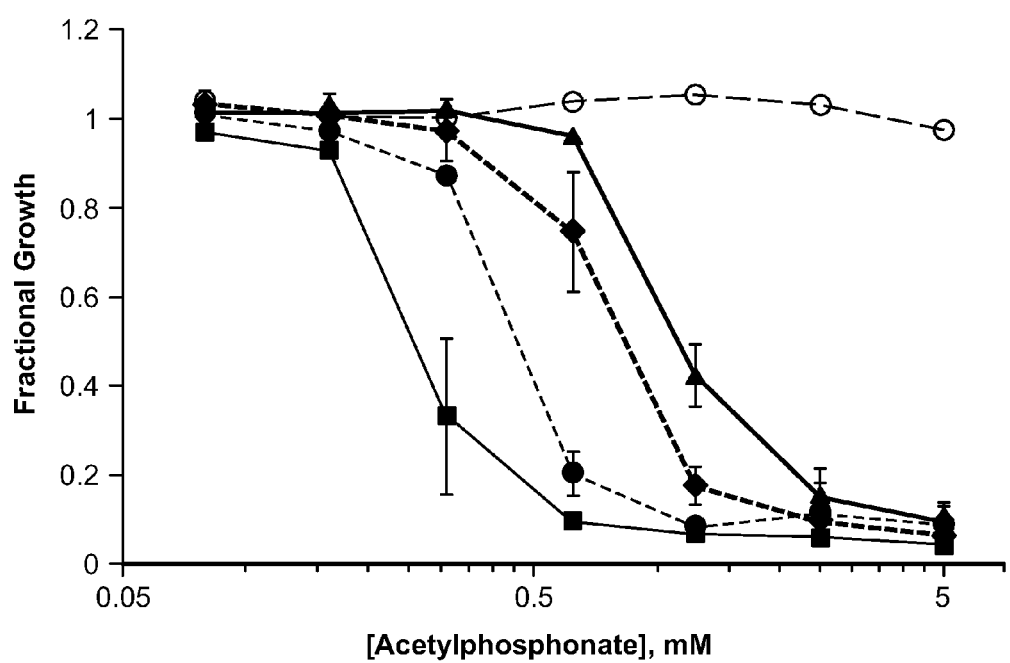
FIG. 10 is a chart showing antimicrobial effects of acetylphosphonates against E. coli (MG1655). OctAP (○) is inactive while BnAP (■), PentAP (●), BAP (♦) and HexAP (▲) exert dose-dependent inhibition of E. coli.
Figure 11:
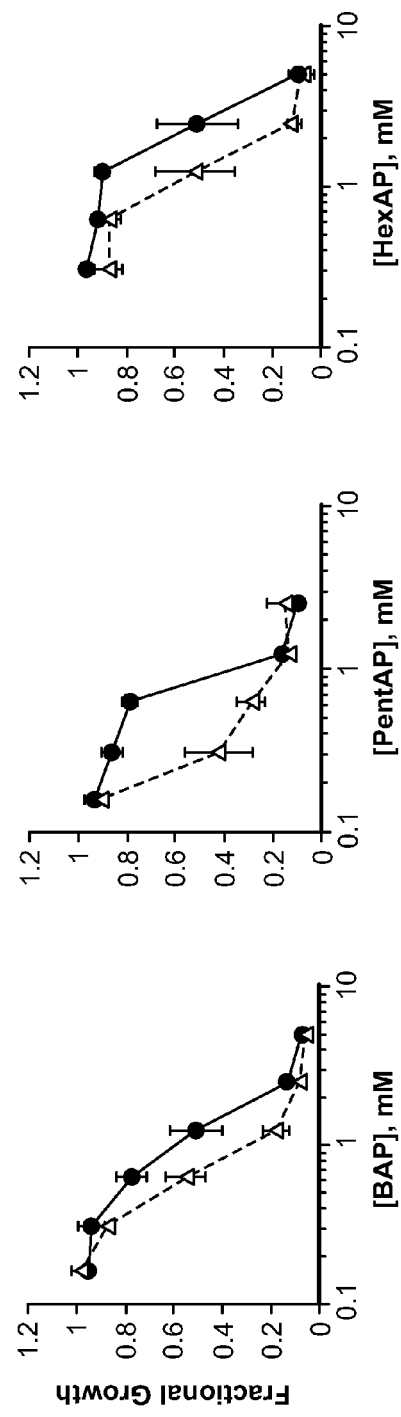
FIG. 11A, FIG. 11B, FIG. 11C, FIG. 11D, FIG. 11E, and FIG. 11F are charts showing that acetylphosphonates are substrates for efflux via the AcrAB-TolC transporter. E. coli BW25113 (●) and the ΔtolC E. coli variant (▲) were treated with BAP (FIG. 11A), PentAP (FIG. 11B), HexAP (FIG. 11C), OctAP (FIG. 11D) and BnAP (FIG. 11E). Fractional growth of E. coli BW25113 (black bars) and the ΔtolC E. coli variant (gray bars) in the presence of 1.25 mM alkylacetylphosphonate (FIG. 11F).
Figure 12:
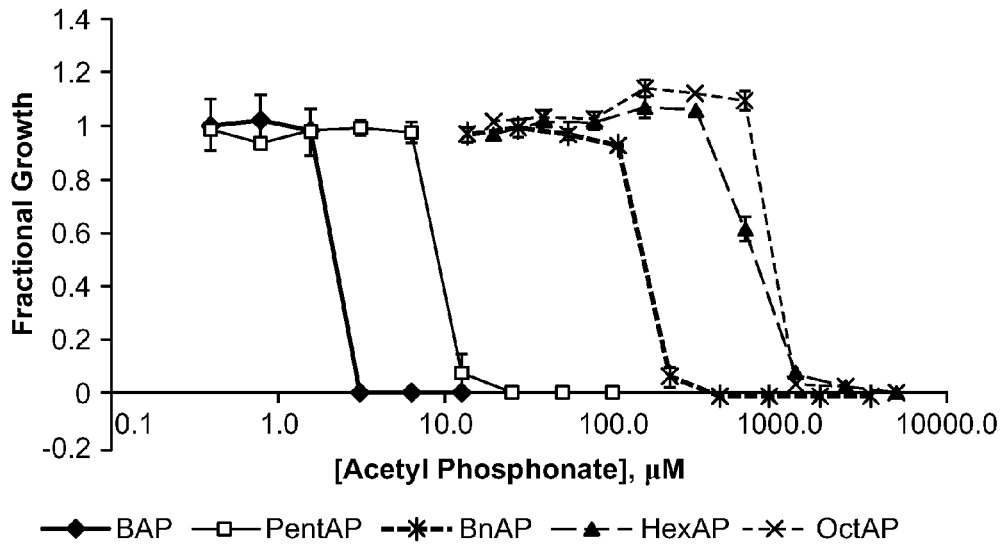
FIG. 12 is a chart showing antimicrobial activity of alkylacetylphosphonates against E. coli K-12 grown in M9 minimal medium.
Figure 13:
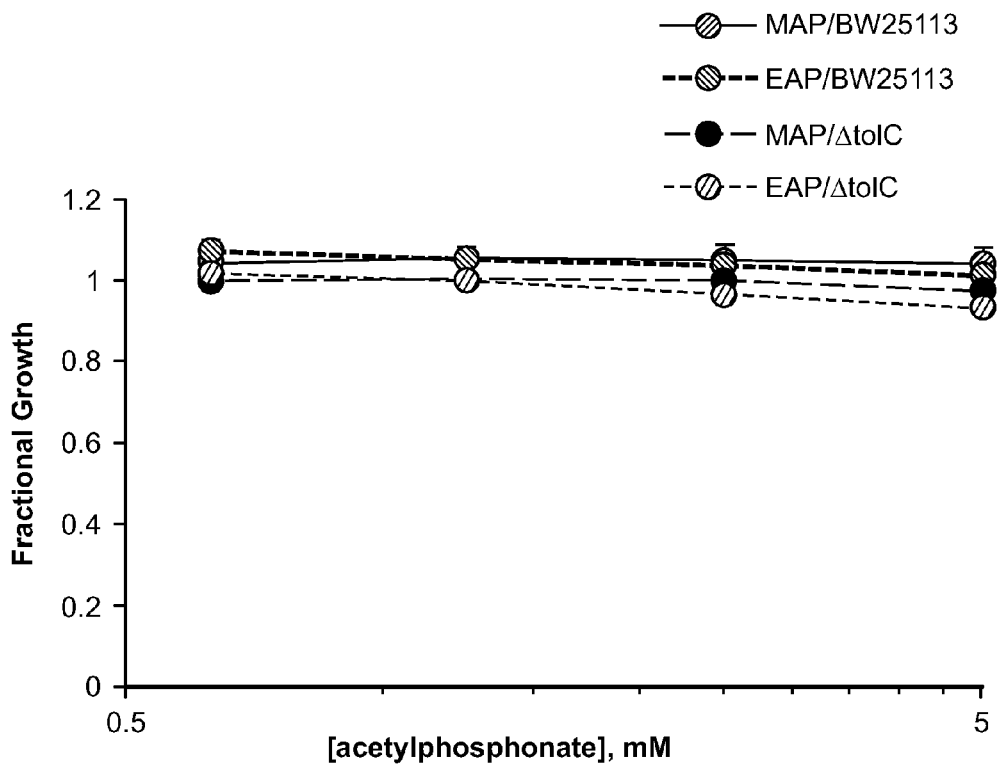
FIG. 13 is a chart showing that MAP (methyl acetylphosphonate) and EAP (ethyl acetylphosphonate) are inactive against E. coli BW25113 and the ΔtolC variant, grown in CAMHB. Standardized innocula of E. coli BW25113 (approximately ~10$^5$ CFU mL$^{-1}$) were treated with varying concentrations of either MAP (blue) or EAP (orange) from 0.63 to 5 mM for 16 hours, and fractional growth was determined by comparison to a no drug control. The ΔtolC variant of BW25113 was also treated with varying concentrations of MAP (black) or EAP (green) from 0.63 to 5 mM for 16 hour, and fractional growth was determined by comparison to no drug controls. Experiments were performed in duplicate, and error bars represent standard deviation.
Figure 15A:
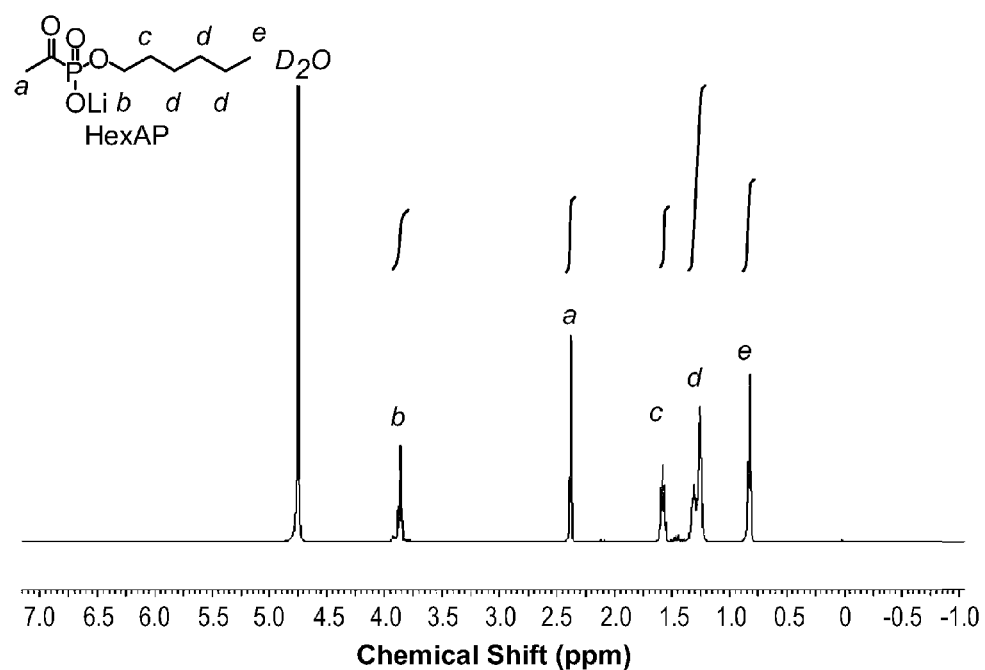
FIG. 15A and FIG. 15B are NMR characterization of HexAP by $^1$H NMR (FIG. 15A) and $^{31}$P NMR (FIG. 15B).
Figure 15B:
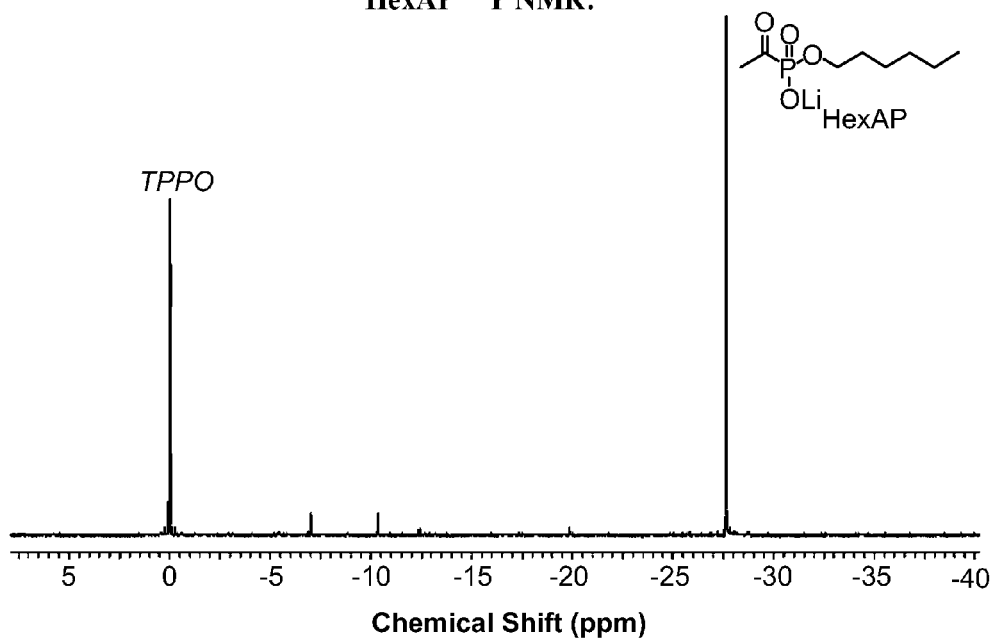

We hypothesized that increasing the alkyl chain length on the AP scaffold would also lead to increased selectivity of inhibition against DXP synthase over PDH as DXP synthase possess a larger active site compared to PDH and other related ThDP-dependent enzymes. Thus, we evaluated the inhibitory activity of PentAP, HexAP and OctAP against PDH (FIG. 6). Contrary to our expectations, PentAP, HexAP and OctAP display comparable or lower $K_i$ values against PDH compared to BAP (Table 5). Thus, the selectivity of inhibition against DXP synthase over PDH decreases modestly with increasing alkyl chain length.
Antimicrobial Activity of Alkylacetylphosphonates Against *E. coli* K-12 Grown in CAMHB As was previously reported, BAP exhibits weak antimicrobial activity by a mechanism involving inhibition of DXP synthase. Thus, BnAP, PentAP, HexAP and OctAP, also shown to inhibit DXP synthase, were evaluated for antimicrobial activity against wild-type K-12 *E. coli* (ATCC: MG1655) grown in rich medium (CAMHB). Despite the observation that acetylphosphonate analogs tested here exhibit comparable low micromolar inhibitory activity against DXP synthase (Table 5), only BnAP, BAP, PentAP and HexAP exert a dose-dependent delay in the growth of *E. coli* (FIG. 7A and FIG. 7B; FIG. 10); OctAP is inactive against wild-type K-12 *E. coli* up to 5 mM (1210 ug/mL) when cells are grown in rich medium (CAMHB). In terms of minimum inhibitory concentration ($MIC_{90}$), PentAP ($MIC^{PentAP}$=1.25 mM) displays somewhat more potent antimicrobial activity compared to BAP ($MIC^{BAP}$=2.5 mM), whereas BnAP exerts the most potent antimicrobial activity in this series ($MIC^{BnAP}$=0.63 mM), and HexAP displays markedly less potent antimicrobial effects $MIC^{HexAP}$=5 mM) against *E. coli* compared to BnAP, BAP or PentAP. As expected, increasing intracellular levels of active DXP synthase results in partial rescue of *E. coli* growth in the presence of BnAP, PentAP and HexAP (FIG. 8), indicating DXP synthase is a likely intracellular target of these acetylphosphonates. DXP synthase overproduction also appears to protect *E. coli* cells from the weak antimicrobial effects of OctAP observed under these growth conditions (FIG. 8).
OctAP is Susceptible to Efflux Via AcrAB-TolC from *E. coli* Grown in CAMHB Data suggest that small acetylphosphonates MAP and EAP are not readily taken up into *E. coli* grown in CAMHB (FIG. 13). Increasing alkyl chain length (BAP and PentAP) appears to enhance permeability and antimicrobial activity. However, these antimicrobial effects are increasingly offset by efflux (OctAP) which lowers the intracellular acetylphosphonate concentration (FIG. 11F). The most dramatic effect of deleting TolC is observed with OctAP (FIG. 11D), supporting the idea that increasing hydrophobicity of the acetylphosphonates seems to increase susceptibility to efflux. However, deletion of the TolC component of the AcrAB-TolC transporter fails to restore antimicrobial activity to micromolar levels observed for these compounds in biochemical inhibition experiments (Table 5). Growth in rich medium may account for this, or inefficient uptake.
Antimicrobial Activity of Alkylacetylphosphonates Against *E. coli* K-12 Grown in M9 Minimal Medium The product of DXP synthase, DXP, lies at a metabolic branchpoint. DXP serves as precursor not only for essential isoprenoids, but also is essential to central metabolism as a precursor to both thiamin diphosphate and pyridoxal phosphate. Thus, evaluation of antimicrobial activity of DXP synthase inhibitors in the standard, rich growth medium (CAMHB) which contains rescuing metabolites, likely underestimates the antimicrobial activities of these agents. Standard in vitro culture conditions may have poor predictive value for these agents in vivo; access to most nutrients is thought to be more difficult from the host than in nutrient rich media. In our preliminary evaluation of acetylphosphonate antimicrobial activity against *E. coli* K-12 (BW25113) grown in M9 minimal medium, we show significantly enhanced antimicrobial activity of BAP (MIC=3.1 mM) and PentAP (MIC=12.5 mM) (FIG. 12). A modest enhancement in the antimicrobial activity of BnAP (MIC=218 mM in M9 compared to 630 mM in CAMHB) is observed. HexAP activity is comparable in M9 minimal medium and CAMHB, and OctAP activity in M9 minimal medium (MIC=1.25 mM) appears to be enhanced relative to its activity in CAMHB growth medium (FIG. 12). These preliminary results suggest the smaller acetylphosphonates may be promising antimicrobial agents targeting central metabolism, and studies to verify intracellular target are underway.

DXP synthase represents an attractive drug target for the development of new anti-infective agents, and selective inhibitors of this enzyme are sought. The present study highlights C—N bond formation as a new reaction catalyzed by DXP synthase and demonstrates nitroso substrates as useful tools for probing the active site of this potential drug target. The study shows that DXP synthase-catalyzed C—N bond formation leads to the generation of hydroxamic acids and amides, with electron rich nitroso substrates giving predominantly amide products. Although the mechanism for this transformation is not elucidated, it is thought to occur via a hydroxamic acid intermediate. [25] Notably, demonstrated herein are results showing that nitroso substrate analogs bearing a naphthol scaffold exhibit exceptional affinity for DXP synthase that is comparable to the natural acceptor substrate, D-GAP. Further, sterically demanding substrates are selectively turned over by DXP synthase and show considerably lower affinity for the ThDP-dependent enzyme PDH. Consistent with this finding, active site volume calculations indicate the DXP synthase active site is significantly larger compared to PDH or transketolase and can uniquely accommodate sterically demanding alternative substrates. The alternative acceptor substrates tested in this study are surprisingly weak inhibitors of DXP formation with nitrosonaphthol 5 acting as a weak competitive inhibitor against D-GAP. The >10-fold discrepancy between $K_m$ and $K_i$ for this compound could suggest multiple binding modes are possible for 5, or could reflect a lower affinity complex en route to a higher affinity ternary complex (described by $K_m^{nitrosonaphthol}$). Evidence that nitrosonaphthols adopt a distinct binding mode to D-GAP during turnover was obtained through substitution of R478 and R420, active site residues essential for D-GAP binding. R478A and R420A variants display efficient turnover and comparable affinity for nitrosonaphthols compared to wild type DXP synthase.

Taken together, the data suggest that incorporation of an aromatic group (or other bulky groups) into an unnatural bisubstrate analog scaffold should serve to impart selectivity of inhibition against DXP synthase over other ThDP-dependent enzymes. Indeed, benzylacetylphosphonate selectively inhibits DXP synthase with a $K_i$ of 10.4±1.3 μM and $K_i^{PDH}/K_i^{DXPS}$ ~85. Although comparable in inhibitory activity to butylacetylphosphonate, [18] an increase in $K_i^{PDH}/K_i^{DXPS}$ is observed with BnAP, suggesting sterically demanding aromatic acetylphosphonates as a promising new class of selective DXP synthase inhibitors.

REFERENCES

[1] C. A. Testa, M. J. Brown, Curr. Pharm. Biotechnol. 2003, 4, 248-259.
[2] H. Jomaa, J. Wiesner, S. Sanderbrand, B. Altincicek, C. Weidemeyer, M. Hintz, I. Turbachova, M. Eberl, J. Zeidler, H. K. Lichtenthaler, D. Soldati, E. Beck, Science 1999, 285, 1573-1576.
[3] M. Rohmer, M. Knani, P. Simonin, B. Sutter, H. Sahm, Biochem. J. 1993, 295 (Pt 2), 517-524.
[4] G. A. Sprenger, U. Schörken, T. Wiegert, S. Grolle, A. A. de Graaf, S. V. Taylor, T. P. Begley, S. Bringer-Meyer, H. Sahm, Proc. Natl. Acad. Sci. U.S.A. 1997, 94, 12857-12862.
[5] T. Kuzuyama, M. Takagi, S. Takahashi, H. Seto, J. Bacteriol. 2000, 182, 891-897.
[6] J. M. Estevez, A. Cantero, A. Reindl, S. Reichler, P. Leon, J. Biol. Chem. 2001, 276, 22901-22909.
[7] M. Harker, P. M. Bramley, FEBS Lett. 1999, 448, 115-119.
[8] A. C. Brown, M. Eberl, D. C. Crick, H. Jomaa, T. Parish, J. Bacteriol. 2010, 192, 2424-2433.
[9] L. M. Lois, N. Campos, S. R. Putra, K. Danielsen, M. Rohmer, A. Boronat, Proc. Natl. Acad. Sci. U.S.A. 1998, 95, 2105-2110.
[10] R. E. Hill, K. Himmeldirk, I. A. Kennedy, R. M. Pauloski, B. G. Sayer, E. Wolf, I. D. Spenser, J. Biol. Chem. 1996, 271, 30426-30435.
[11] L. M. Eubanks, C. D. Poulter, Biochemistry 2003, 42, 1140-1149.
[12] H. Patel, N. S. Nemeria, L. A. Brammer, C. L. Freel Meyers, F. Jordan, J. Am. Chem. Soc. 2012, 134, 18374-18379.
[13] L. A. Brammer, J. M. Smith, H. Wade, C. F. Meyers, J. Biol. Chem. 2011, 286, 36522-36531.
[14] R. A. Frank, F. J. Leeper, B. F. Luisi, Cell Mol. Life Sci. 2007, 64, 892-905.
[15] R. Kluger, K. Tittmann, Chem. Rev. 2008, 108, 1797-1833.
[16] S. Xiang, G. Usunow, G. Lange, M. Busch, L. Tong, J. Biol. Chem. 2007, 282, 2676-2682.
[17] J. Mao, H. Eoh, R. He, Y. Wang, B. Wan, S. G. Franzblau, D. C. Crick, A. P. Kozikowski, Bioorg. Med. Chem. Lett. 2008, 18, 5320-5323.
[18] J. M. Smith, R. J. Vierling, C. F. Meyers, MedChemComm 2012, 3, 65-67.
[19] L. A. Brammer, C. F. Meyers, Org. Lett. 2009, 11, 4748-4751.
[20] M. Pohl, B. Lingen, M. Müller, Chemistry 2002, 8, 5288-5295.
[21] M. Mueller, D. Gocke, M. Pohl, Febs J. 2009, 276, 2894-2904.
[22] A. S. Demir, P. Ayhan, S. B. Sopaci, Clean-Soil Air Water 2007, 35, 406-412.
[23] M. D. Corbett, J. E. Cahoy, B. R. Chipko, J. Natl. Cancer Inst. 1975, 55, 1247-1248.
[24] M. D. Corbett, B. R. Chipko, Bioorg. Chem. 1980, 9, 273-287.
[25] M. D. Corbett, B. R. Corbett, Bioorg. Chem. 1982, 11, 328-337.
[26] M. D. Corbett, B. R. Corbett, Biochem. Pharmacol. 1986, 35, 3613-3621.
[27] a) T. Yoshioka, T. Uematsu, Biochem. J. 1993, 290 (Pt 3), 783-790; b) P. Ayhan, A. S. Demir, Advanced Synthesis & Catalysis 2011, 353, 624-629.
[28] P. Emsley, K. Cowtan, Acta Cryst D 2004, 60, 2126-2132.
[29] M. Hendlich, F. Rippmann, G. Barnickel, J. Mol. Graph. Model. 1997, 15, 359-363.
[30] V. Le Guilloux, P. Schmidtke, P. Tuffery, BMC Bioinformatics 2009, 10, 168-2105-10-168.
[31] O. D. Monera, T. J. Sereda, N. E. Zhou, C. M. Kay, R. S. Hodges, J. Pept. Sci. 1995, 1, 319-329.
[32] M. Yoshida, A. Akane, Anal. Chem. 1999, 71, 1918-1921.
[33] M. Kato, R. M. Wynn, J. L. Chuang, S. C. Tso, M. Machius, J. Li, D. T. Chuang, Structure 2008, 16, 1849-1859.
[34] L. Mitschke, C. Parthier, K. Schröder-Tittmann, J. Coy, S. Ludtke, K. Tittmann, J. Biol. Chem. 2010, 285, 31559-31570.
[35] W. Humphrey, A. Dalke, K. Schulten, J. Molec. Graphics 1996, 14, 33-38.
[36] E. Krissinel, K. Henrick, J. Mol. Biol. 2007, 372, 774.
[37] M. Saady, L. Lebeau, C. Mioskowski, Helv. Chim. Acta 1995, 78, 670-678.
[38] S. Strumilo, J. Czerniecki, P. Dobrzyn, Biochem. Biophys. Res. Commun. 1999, 256, 341-345.
[39] F. Morris et al., ChemBioChem. 2013, 14, 1309-1315.
[40] J. M. Smith et al., The Journal of Antibiotics 2014, 67, 77-83.

The disclosures of each and every patent, patent application, and publication cited herein are hereby incorporated herein by reference in their entirety.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

What is claimed is:

1. A pharmaceutical composition comprising a compound represented by the formula:

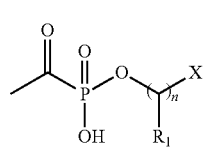
(I)
in which
X is phenyl;
R₁, independently is absent, or if present, is halo or optionally substituted $C_1$-$C_4$ alkyl; and,
n is 1;
or a pharmaceutically acceptable salt thereof, together with a pharmaceutically acceptable carrier.
2. The pharmaceutical composition of claim 1, wherein the pharmaceutical composition comprises:
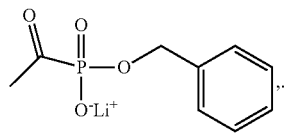
* * * * *

UNITED STATES PATENT AND TRADEMARK OFFICE
CERTIFICATE OF CORRECTION

PATENT NO.         : 9,930,893 B2
APPLICATION NO.    : 14/618589
DATED              : April 3, 2018
INVENTOR(S)        : Caren L. Freel Meyers et al.

It is certified that error appears in the above-identified patent and that said Letters Patent is hereby corrected as shown below:

In the Specification

Column 1 Lines 11-16, please replace the second paragraph as follows:
STATEMENT OF GOVERNMENTAL INTEREST
This invention was made with government support under grant numbers GM084998, GM080189, awarded by the National Institutes of Health. The government has certain rights in the invention.

Signed and Sealed this
Thirteenth Day of November, 2018

Andrei Iancu
*Director of the United States Patent and Trademark Office*